(12) United States Patent
Haggstrom et al.

(10) Patent No.: US 10,201,644 B2
(45) Date of Patent: Feb. 12, 2019

(54) SELF CONTAINED WOUND DRESSING WITH MICROPUMP

(71) Applicant: SMITH & NEPHEW, INC., Memphis, TN (US)

(72) Inventors: Kurt Haggstrom, Huntington Beach, CA (US); Alain Tranchemontagne, Warwick, RI (US); Loredana Jinga, North Attleboro, MA (US)

(73) Assignee: Smith & Nephew, Inc., Memphis, TN (US)

( * ) Notice: Subject to any disclaimer, the term of this patent is extended or adjusted under 35 U.S.C. 154(b) by 1158 days.

(21) Appl. No.: 14/480,537

(22) Filed: Sep. 8, 2014

(65) Prior Publication Data
US 2015/0065965 A1 Mar. 5, 2015

Related U.S. Application Data

(60) Continuation of application No. 13/483,109, filed on May 30, 2012, now Pat. No. 8,829,263, which is a
(Continued)

(51) Int. Cl.
*A61M 1/00* (2006.01)
*A61F 13/00* (2006.01)
(Continued)

(52) U.S. Cl.
CPC ....... *A61M 1/009* (2014.02); *A61F 13/00055* (2013.01); *A61F 13/00063* (2013.01);
(Continued)

(58) Field of Classification Search
CPC .... A61M 1/009; A61M 1/0027; A61M 27/00; A61M 1/0088; A61M 1/0031;
(Continued)

(56) References Cited

U.S. PATENT DOCUMENTS

| 695,270 A | 3/1902 | Beringer |
|---|---|---|
| 1,480,562 A | 1/1924 | Mock |

(Continued)

FOREIGN PATENT DOCUMENTS

| CA | 2 198 243 | 2/1996 |
|---|---|---|
| CA | 2 367 460 | 10/2000 |

(Continued)

OTHER PUBLICATIONS

US 6,216,701, 04/2001, Heaton et al. (withdrawn)
(Continued)

*Primary Examiner* — Tarla R Patel
(74) *Attorney, Agent, or Firm* — Knobbe, Martens, Olson & Bear, LLP

(57) ABSTRACT

A composite wound dressing apparatus promotes healing of a wound via the use of a micropump system housed within or above a wound dressing member. The micropump system includes a miniature pump that applies a subatmospheric pressure to the wound to effectively draw wound fluid or exudate away from the wound bed without the need for a cumbersome external vacuum source. Hence, the wound dressing and micropump system is portable which allows the patient mobility that is unavailable when an external vacuum source is used. The patient does not need to be constrained for any period of time while exudate is being removed from the wound.

42 Claims, 7 Drawing Sheets

Related U.S. Application Data continuation of application No. 12/917,103, filed on Nov. 1, 2010, now Pat. No. 8,207,392, which is a division of application No. 12/496,263, filed on Jul. 1, 2009, now Pat. No. 7,838,717, which is a continuation of application No. 11/517,210, filed on Sep. 6, 2006, now Pat. No. 7,569,742.

(60) Provisional application No. 60/714,812, filed on Sep. 6, 2005.

(51) Int. Cl.
*A61F 13/02* (2006.01)
*A61M 27/00* (2006.01)

(52) U.S. Cl.
CPC .... *A61F 13/00068* (2013.01); *A61F 13/0203* (2013.01); *A61F 13/023* (2013.01); *A61M 1/0027* (2014.02); *A61M 1/0031* (2013.01); *A61M 1/0088* (2013.01); *A61M 27/00* (2013.01); *A61F 2013/0057* (2013.01); *A61F 2013/0091* (2013.01); *A61F 2013/00174* (2013.01); *A61F 2013/00182* (2013.01); *A61F 2013/00553* (2013.01); *A61F 2013/00846* (2013.01); *A61F 2013/00927* (2013.01); *A61F 2013/00944* (2013.01); *A61F 2013/00957* (2013.01); *A61M 2205/15* (2013.01); *A61M 2205/3592* (2013.01); *A61M 2205/8206* (2013.01)

(58) Field of Classification Search
CPC .......... A61M 2205/15; A61F 13/00068; A61F 13/00055; A61F 13/00063; A61F 13/0203; A61F 13/023; A61F 2013/00957; A61F 2013/00944
USPC ..... 128/888; 206/288, 289, 313, 315; 602/2, 602/41–43, 53–54; 424/443–449; 604/304, 305, 307–308, 313, 315, 543, 604/521, 48, 500, 503, 505, 176, 289–290
See application file for complete search history.

(56) References Cited

U.S. PATENT DOCUMENTS

| | | |
|---|---|---|
| 2,280,915 A | 4/1942 | Johnson |
| 2,367,690 A | 7/1943 | Purdy |
| 2,568,933 A | 9/1951 | Robbins |
| 2,632,443 A | 3/1953 | Lesher |
| 2,682,873 A | 7/1954 | Evans et al. |
| 2,905,174 A | 9/1959 | Smith |
| 3,367,332 A | 2/1968 | Groves |
| 3,486,504 A | 12/1969 | Austin, Jr. |
| 3,572,340 A | 3/1971 | Lloyd et al. |
| 3,610,238 A | 10/1971 | Rich, Jr. |
| 3,687,136 A | 8/1972 | Carmody |
| 3,712,298 A | 1/1973 | Snowdon et al. |
| 3,809,086 A | 5/1974 | Schachet et al. |
| 3,874,387 A | 4/1975 | Barbieri |
| 3,963,029 A | 6/1976 | Brooks |
| 3,972,328 A | 8/1976 | Chen |
| 3,993,080 A | 11/1976 | Loseff |
| 4,029,598 A | 6/1977 | Neisius et al. |
| RE29,319 E | 7/1977 | Nordby et al. |
| 4,080,970 A | 3/1978 | Miller |
| 4,102,342 A | 7/1978 | Akiyama et al. |
| 4,112,947 A | 9/1978 | Nehring |
| 4,112,949 A | 9/1978 | Rosenthal et al. |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,250,882 A | 2/1981 | Adair |
| 4,266,545 A | 5/1981 | Moss |
| 4,316,466 A | 2/1982 | Babb |
| 4,382,441 A | 5/1983 | Svedman |
| 4,398,910 A | 8/1983 | Blake et al. |
| 4,465,485 A | 8/1984 | Kashmer et al. |
| 4,468,227 A | 8/1984 | Jensen |
| 4,524,064 A | 6/1985 | Nambu |
| 4,525,166 A | 6/1985 | Leclerc |
| 4,534,356 A | 8/1985 | Papadakis |
| 4,551,141 A | 11/1985 | McNeil |
| 4,573,965 A | 3/1986 | Russo |
| 4,608,041 A | 8/1986 | Nielsen |
| 4,655,754 A | 4/1987 | Richmond et al. |
| 4,655,766 A | 4/1987 | Theeuwes et al. |
| 4,681,562 A | 7/1987 | Beck et al. |
| 4,710,165 A | 12/1987 | McNeil et al. |
| 4,743,232 A | 5/1988 | Kruger |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,798,603 A | 1/1989 | Meyer et al. |
| 4,813,942 A | 3/1989 | Alvarez |
| 4,820,284 A | 4/1989 | Hauri |
| 4,826,494 A | 5/1989 | Richmond et al. |
| 4,834,735 A | 5/1989 | Alemany et al. |
| 4,846,164 A | 7/1989 | Martz |
| 4,921,488 A | 5/1990 | Maitz et al. |
| 4,936,834 A | 6/1990 | Beck et al. |
| 4,950,483 A | 8/1990 | Ksander et al. |
| 4,968,181 A | 11/1990 | Goldman |
| 4,969,880 A | 11/1990 | Zamierowski |
| 4,972,829 A | 11/1990 | Knerr |
| 4,973,325 A | 11/1990 | Sherrod et al. |
| 4,979,944 A | 12/1990 | Luzsicza |
| 4,988,344 A | 1/1991 | Reising et al. |
| 4,988,345 A | 1/1991 | Reising |
| 4,990,137 A | 2/1991 | Graham |
| 4,994,022 A | 2/1991 | Steffler et al. |
| 4,997,438 A | 3/1991 | Nipper |
| 5,018,515 A | 5/1991 | Gilman |
| 5,021,050 A | 6/1991 | Iskra |
| 5,055,195 A | 10/1991 | Trasch et al. |
| 5,055,198 A | 10/1991 | Shettigar |
| 5,056,510 A | 10/1991 | Gilman |
| 5,065,600 A | 11/1991 | Byles |
| 5,071,409 A | 12/1991 | Rosenberg |
| 5,073,172 A | 12/1991 | Fell |
| 5,100,395 A | 3/1992 | Rosenberg |
| 5,100,396 A | 3/1992 | Zamierowski |
| 5,106,629 A | 4/1992 | Cartmell et al. |
| 5,115,801 A | 5/1992 | Cartmell et al. |
| 5,124,197 A | 6/1992 | Bernardin et al. |
| 5,141,503 A | 8/1992 | Sewell, Jr. |
| 5,149,331 A | 9/1992 | Ferdman et al. |
| 5,149,334 A | 9/1992 | Lahrman et al. |
| 5,151,091 A | 9/1992 | Glaug et al. |
| 5,152,757 A | 10/1992 | Eriksson |
| 5,160,322 A | 11/1992 | Scheremet et al. |
| 5,160,328 A | 11/1992 | Cartmell et al. |
| 5,167,613 A | 12/1992 | Karami et al. |
| 5,171,391 A | 12/1992 | Chmielewski et al. |
| 5,175,046 A | 12/1992 | Nguyen |
| 5,176,663 A | 1/1993 | Svedman et al. |
| 5,178,157 A | 1/1993 | Fanlo |
| 5,181,905 A | 1/1993 | Flam |
| 5,195,977 A | 3/1993 | Pollitt |
| 5,197,945 A | 3/1993 | Cole et al. |
| 5,215,519 A | 6/1993 | Shettigar |
| 5,217,445 A | 6/1993 | Young et al. |
| 5,234,419 A | 8/1993 | Bryant et al. |
| 5,236,427 A | 8/1993 | Hamajima et al. |
| 5,238,732 A | 8/1993 | Krishnan |
| 5,242,435 A | 9/1993 | Murji et al. |
| 5,257,982 A | 11/1993 | Cohen et al. |
| 5,261,893 A | 11/1993 | Zamierowski |
| 5,263,922 A | 11/1993 | Soya et al. |
| 5,266,928 A | 11/1993 | Johnson |

(56) References Cited

U.S. PATENT DOCUMENTS

| | | |
|---|---|---|
| 5,271,987 A | 12/1993 | Iskra |
| 5,279,608 A | 1/1994 | Cherif Cheikh |
| 5,281,208 A | 1/1994 | Thompson et al. |
| 5,294,478 A | 3/1994 | Wanek et al. |
| 5,296,290 A | 3/1994 | Brassington |
| 5,314,743 A | 5/1994 | Meirowitz et al. |
| 5,318,554 A | 6/1994 | Young et al. |
| 5,328,614 A | 7/1994 | Matsumura |
| 5,330,456 A | 7/1994 | Robinson |
| 5,336,219 A | 8/1994 | Krantz |
| 5,342,336 A | 8/1994 | Meirowitz et al. |
| 5,348,547 A | 9/1994 | Payne et al. |
| 5,354,261 A | 10/1994 | Clark et al. |
| 5,356,405 A | 10/1994 | Thompson et al. |
| 5,358,494 A | 10/1994 | Svedman |
| 5,360,420 A | 11/1994 | Cook et al. |
| 5,364,381 A | 11/1994 | Soga et al. |
| 5,364,382 A | 11/1994 | Latimer et al. |
| 5,366,451 A | 11/1994 | Levesque |
| 5,368,909 A | 11/1994 | Langdon et al. |
| 5,368,926 A | 11/1994 | Thompson et al. |
| 5,374,260 A | 12/1994 | Lemay et al. |
| 5,380,280 A | 1/1995 | Peterson |
| 5,380,294 A | 1/1995 | Persson |
| 5,382,245 A | 1/1995 | Thompson et al. |
| 5,387,208 A | 2/1995 | Ashton et al. |
| 5,397,316 A | 3/1995 | LaVon et al. |
| 5,401,267 A | 3/1995 | Couture-Dorschner et al. |
| 5,425,725 A | 6/1995 | Tanzer et al. |
| 5,431,643 A | 7/1995 | Ouellette et al. |
| 5,437,651 A | 8/1995 | Todd et al. |
| 5,445,604 A | 8/1995 | Lang |
| 5,447,492 A | 9/1995 | Cartmell et al. |
| 5,454,800 A | 10/1995 | Hirt et al. |
| 5,456,660 A | 10/1995 | Reich et al. |
| D364,679 S | 11/1995 | Heaton et al. |
| 5,465,735 A | 11/1995 | Patel |
| 5,466,229 A | 11/1995 | Elson |
| 5,470,326 A | 11/1995 | Dabi et al. |
| H1511 H | 12/1995 | Chappell et al. |
| 5,480,377 A | 1/1996 | Cartmell et al. |
| 5,484,427 A | 1/1996 | Gibbons |
| 5,486,167 A | 1/1996 | Dragoo et al. |
| 5,487,736 A | 1/1996 | Van Phan |
| 5,489,280 A | 2/1996 | Russell |
| 5,497,788 A | 3/1996 | Inman et al. |
| 5,498,338 A | 3/1996 | Kruger et al. |
| 5,500,270 A | 3/1996 | Langdon et al. |
| 5,505,719 A | 4/1996 | Cohen et al. |
| 5,509,914 A | 4/1996 | Osborn, III |
| 5,514,120 A | 5/1996 | Johnston et al. |
| 5,525,407 A | 6/1996 | Yang |
| 5,527,293 A | 6/1996 | Zamierowski |
| 5,536,233 A | 7/1996 | Khouri |
| 5,536,264 A | 7/1996 | Hsueh et al. |
| 5,538,500 A | 7/1996 | Peterson |
| H1585 H | 8/1996 | Ahr |
| 5,545,155 A | 8/1996 | Hseih et al. |
| 5,549,584 A | 8/1996 | Gross |
| 5,549,589 A | 8/1996 | Horney et al. |
| 5,562,107 A | 10/1996 | Lavender et al. |
| 5,562,646 A | 10/1996 | Goldman et al. |
| 5,562,650 A | 10/1996 | Everett et al. |
| 5,579,765 A | 12/1996 | Cox et al. |
| 5,588,958 A | 12/1996 | Cunningham et al. |
| 5,591,148 A | 1/1997 | McFall et al. |
| 5,591,149 A | 1/1997 | Cree et al. |
| 5,603,707 A | 2/1997 | Trombetta et al. |
| 5,603,946 A | 2/1997 | Constantine |
| 5,609,588 A | 3/1997 | DiPalma et al. |
| 5,613,960 A | 3/1997 | Mizutani |
| 5,614,283 A | 3/1997 | Pontis et al. |
| 5,614,295 A | 3/1997 | Quincy, III et al. |
| 5,628,736 A | 5/1997 | Thompson |
| 5,632,731 A | 5/1997 | Patel |
| H1657 H | 6/1997 | Hammons et al. |
| 5,634,915 A | 6/1997 | Osterdahl |
| 5,636,643 A | 6/1997 | Argenta et al. |
| 5,637,080 A | 6/1997 | Geng |
| 5,643,189 A | 7/1997 | Masini |
| 5,643,238 A | 7/1997 | Baker |
| 5,645,081 A | 7/1997 | Argenta et al. |
| 5,648,142 A | 7/1997 | Phillips |
| 5,649,915 A | 7/1997 | Chauvette et al. |
| 5,649,916 A | 7/1997 | DiPalma et al. |
| 5,662,599 A | 9/1997 | Reich et al. |
| 5,665,082 A | 9/1997 | Boulanger |
| 5,669,895 A | 9/1997 | Murakami et al. |
| 5,675,079 A | 10/1997 | Gilman et al. |
| 5,678,564 A | 10/1997 | Lawrence et al. |
| 5,700,254 A | 12/1997 | McDowall et al. |
| 5,701,917 A | 12/1997 | Khouri |
| 5,702,356 A | 12/1997 | Hathman |
| 5,704,905 A | 1/1998 | Jensen et al. |
| 5,707,499 A | 1/1998 | Joshi et al. |
| 5,713,384 A | 2/1998 | Roach et al. |
| 5,716,703 A | 2/1998 | Payne |
| 5,728,084 A | 3/1998 | Palumbo et al. |
| 5,728,085 A | 3/1998 | Widlund et al. |
| 5,733,273 A | 3/1998 | Ahr |
| 5,733,305 A | 3/1998 | Fleischmann |
| 5,733,337 A | 3/1998 | Carr et al. |
| 5,752,945 A | 5/1998 | Mosley et al. |
| 5,759,570 A | 6/1998 | Arnold |
| 5,762,641 A | 6/1998 | Bewick-Sonntag et al. |
| 5,779,657 A | 7/1998 | Daneshvar |
| 5,785,688 A | 7/1998 | Joshi et al. |
| 5,788,684 A | 8/1998 | Abuto et al. |
| 5,801,107 A | 9/1998 | Everhart et al. |
| 5,810,798 A | 9/1998 | Finch et al. |
| 5,817,081 A | 10/1998 | LaVon et al. |
| 5,827,213 A | 10/1998 | Jensen |
| 5,827,254 A | 10/1998 | Trombetta et al. |
| 5,830,202 A | 11/1998 | Bogdanski et al. |
| 5,830,496 A | 11/1998 | Freeman |
| 5,833,646 A | 11/1998 | Masini |
| 5,837,627 A | 11/1998 | Halabisky et al. |
| 5,840,049 A | 11/1998 | Tumey et al. |
| 5,840,052 A | 11/1998 | Johns |
| 5,843,011 A | 12/1998 | Lucas |
| 5,843,025 A | 12/1998 | Shaari |
| 5,843,064 A | 12/1998 | Koczab |
| 5,855,572 A | 1/1999 | Schmidt |
| 5,865,822 A | 2/1999 | Hamajima et al. |
| 5,865,824 A | 2/1999 | Chen et al. |
| 5,868,933 A | 2/1999 | Patrick et al. |
| 5,873,867 A | 2/1999 | Coles et al. |
| 5,876,611 A | 3/1999 | Shettigar |
| 5,877,097 A | 3/1999 | West et al. |
| 5,895,379 A | 4/1999 | Litchholt et al. |
| 5,897,541 A | 4/1999 | Uitenbrock et al. |
| 5,981,120 A | 4/1999 | Chmielewski |
| 5,911,222 A | 6/1999 | Lawrence et al. |
| 5,916,507 A | 6/1999 | Dabi et al. |
| 5,925,026 A | 7/1999 | Arteman et al. |
| 5,931,823 A | 8/1999 | Stokes et al. |
| 5,938,995 A | 8/1999 | Koltisko, Jr. et al. |
| 5,941,863 A | 8/1999 | Guidotti et al. |
| 5,944,703 A | 8/1999 | Dixon et al. |
| 5,947,945 A | 9/1999 | Cree et al. |
| 5,951,535 A | 9/1999 | Fujiwara et al. |
| 5,961,506 A | 10/1999 | Guidotti et al. |
| 5,964,723 A | 10/1999 | Augustine |
| 5,968,027 A | 10/1999 | Cole et al. |
| 5,989,478 A | 11/1999 | Ouellette et al. |
| 6,010,524 A | 1/2000 | Fleischmann |
| 6,022,610 A | 2/2000 | Phan et al. |
| 6,037,518 A | 3/2000 | Guidotti et al. |
| 6,040,493 A | 3/2000 | Cooke et al. |
| 6,060,638 A | 5/2000 | Paul et al. |
| 6,068,620 A | 5/2000 | Chmielewski |
| 6,071,267 A | 6/2000 | Zamierowski |
| 6,075,177 A | 6/2000 | Bahia et al. |
| 6,077,526 A | 6/2000 | Scully et al. |

(56) References Cited

U.S. PATENT DOCUMENTS

| | | |
|---|---|---|
| 6,096,015 A | 8/2000 | Yeo et al. |
| 6,103,951 A | 8/2000 | Freeman |
| 6,103,953 A | 8/2000 | Cree et al. |
| 6,103,954 A | 8/2000 | Grondin et al. |
| 6,107,539 A | 8/2000 | Palumbo et al. |
| 6,110,197 A | 8/2000 | Augustine et al. |
| 6,117,111 A | 9/2000 | Fleischmann |
| 6,117,523 A | 9/2000 | Sugahara |
| 6,124,520 A | 9/2000 | Roberts |
| 6,124,521 A | 9/2000 | Roberts |
| 6,127,595 A | 10/2000 | Makoui et al. |
| 6,135,116 A | 10/2000 | Vogel et al. |
| D434,150 S | 11/2000 | Turney et al. |
| 6,142,982 A | 11/2000 | Hunt et al. |
| 6,156,334 A | 12/2000 | Meyer-Ingold et al. |
| 6,168,800 B1 | 1/2001 | Dobos et al. |
| 6,168,849 B1 | 1/2001 | Braverman et al. |
| 6,174,306 B1 | 1/2001 | Fleischmann |
| 6,176,307 B1 | 1/2001 | Danos et al. |
| 6,183,438 B1 | 2/2001 | Berguer |
| 6,191,340 B1 | 2/2001 | Carlucci et al. |
| 6,203,563 B1 | 3/2001 | Fernandez |
| 6,206,865 B1 | 3/2001 | Chen et al. |
| 6,225,523 B1 | 5/2001 | Masini |
| 6,235,302 B1 | 5/2001 | Mans et al. |
| 6,235,966 B1 | 5/2001 | Magnusson et al. |
| 6,254,567 B1 | 7/2001 | Treu et al. |
| 6,255,552 B1 | 7/2001 | Cummings et al. |
| 6,261,276 B1 | 7/2001 | Reitsma |
| 6,261,283 B1 | 7/2001 | Morgan et al. |
| 6,264,776 B1 | 7/2001 | DiPalma |
| 6,287,521 B1 | 9/2001 | Quay et al. |
| 6,294,710 B1 | 9/2001 | Schmidt et al. |
| 6,297,423 B1 | 10/2001 | Schoenfeldt et al. |
| 6,325,788 B1 | 12/2001 | McKay |
| 6,344,036 B1 | 2/2002 | Ivansson |
| 6,345,623 B1 | 2/2002 | Heaton et al. |
| 6,348,423 B1 | 2/2002 | Griffiths et al. |
| 6,362,390 B1 | 3/2002 | Carlucci et al. |
| 6,369,292 B1 | 4/2002 | Strack et al. |
| 6,372,952 B1 | 4/2002 | Lash et al. |
| 6,398,767 B1 | 6/2002 | Fleischmann |
| 6,402,724 B1 | 6/2002 | Smith et al. |
| 6,403,857 B1 | 6/2002 | Gross et al. |
| 6,406,447 B1 | 6/2002 | Thrash et al. |
| 6,420,622 B1 | 7/2002 | Johnston et al. |
| 6,440,167 B2 | 8/2002 | Shimizu |
| 6,450,773 B1 | 9/2002 | Upton |
| 6,458,109 B1 | 10/2002 | Henley et al. |
| 6,461,339 B1 | 10/2002 | Sugahara |
| 6,465,708 B1 | 10/2002 | Augustine |
| 6,471,685 B1 | 10/2002 | Johnson |
| 6,471,982 B1 | 10/2002 | Lydon et al. |
| 6,482,491 B1 | 11/2002 | Samuelsen et al. |
| 6,488,643 B1 | 12/2002 | Tumey et al. |
| 6,491,684 B1 | 12/2002 | Joshi et al. |
| 6,497,689 B1 | 12/2002 | Schmidt et al. |
| 6,500,112 B1 | 12/2002 | Khouri |
| 6,506,175 B1 | 1/2003 | Goldstein |
| 6,506,960 B1 | 1/2003 | Young et al. |
| 6,520,982 B1 | 2/2003 | Boynton et al. |
| 6,521,813 B1 | 2/2003 | Chihani |
| 6,528,696 B1 | 3/2003 | Ireland |
| 6,534,149 B1 | 3/2003 | Daley et al. |
| 6,545,194 B1 | 4/2003 | Schmidt et al. |
| 6,551,295 B1 | 4/2003 | Schmidt et al. |
| 6,552,244 B1 | 4/2003 | Jacques et al. |
| 6,553,998 B2 | 4/2003 | Heaton et al. |
| D475,134 S | 5/2003 | Randolph |
| 6,557,704 B1 | 5/2003 | Randolph |
| 6,570,057 B1 | 5/2003 | Schmidt et al. |
| 6,570,058 B1 | 5/2003 | Fuchs et al. |
| 6,573,424 B1 | 6/2003 | Raidel et al. |
| 6,599,262 B1 | 7/2003 | Masini |
| D469,175 S | 8/2003 | Hall et al. |
| D469,176 S | 8/2003 | Hall et al. |
| D478,659 S | 8/2003 | Hall et al. |
| 6,607,495 B1 * | 8/2003 | Skalak ........... A61B 5/411 600/573 |
| 6,610,898 B1 | 8/2003 | Magnusson et al. |
| 6,610,903 B1 | 8/2003 | Latimer et al. |
| 6,613,028 B1 | 9/2003 | Daley et al. |
| 6,613,953 B1 | 9/2003 | Altura |
| 6,613,955 B1 | 9/2003 | Lindsay et al. |
| 6,626,891 B2 | 9/2003 | Ohmstede |
| 6,630,611 B1 | 10/2003 | Malowaniec |
| 6,648,862 B2 | 11/2003 | Watson |
| 6,664,439 B1 | 12/2003 | Arndt et al. |
| 6,673,028 B1 | 1/2004 | Argenta et al. |
| 6,676,610 B2 | 1/2004 | Morton et al. |
| 6,683,229 B1 | 1/2004 | Ehrnsperger et al. |
| 6,685,681 B2 | 2/2004 | Lockwood et al. |
| 6,695,823 B1 | 2/2004 | Lina et al. |
| 6,695,824 B2 | 2/2004 | Howard et al. |
| D488,558 S | 4/2004 | Hall |
| 6,719,742 B1 | 4/2004 | McCormack et al. |
| 6,727,403 B1 | 4/2004 | Ehrnsperger et al. |
| 6,752,794 B2 | 6/2004 | Lockwood et al. |
| 6,755,807 B2 | 6/2004 | Risk, Jr. et al. |
| 6,764,459 B1 | 7/2004 | Donaldson |
| 6,764,462 B2 | 7/2004 | Risk, Jr. et al. |
| 6,767,334 B1 | 7/2004 | Randolph |
| 6,783,837 B1 | 8/2004 | Creagan et al. |
| 6,787,682 B2 | 9/2004 | Gilman |
| 6,794,554 B2 | 9/2004 | Sessions et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,835,192 B1 | 12/2004 | Guidotti et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,960,181 B2 | 11/2005 | Stevens |
| 6,977,323 B1 | 12/2005 | Swenson |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,037,254 B2 | 5/2006 | O'Connor et al. |
| 7,049,478 B1 | 5/2006 | Smith et al. |
| 7,052,167 B2 | 5/2006 | Vanderschuit |
| 7,067,709 B2 | 6/2006 | Murate et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,112,712 B2 | 9/2006 | Ancell |
| 7,117,869 B2 | 10/2006 | Heaton et al. |
| 7,118,545 B2 | 10/2006 | Boyde |
| 7,122,023 B1 | 10/2006 | Hinoki |
| 7,128,719 B2 | 10/2006 | Rosenberg |
| 7,128,735 B2 | 10/2006 | Weston |
| 7,144,390 B1 | 12/2006 | Hanningan et al. |
| 7,169,151 B1 | 1/2007 | Lytinas |
| 7,182,758 B2 | 2/2007 | McCraw |
| 7,195,624 B2 | 3/2007 | Lockwood et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,273,054 B2 | 9/2007 | Heaton et al. |
| 7,276,051 B1 | 10/2007 | Henley et al. |
| 7,279,612 B1 | 10/2007 | Heaton et al. |
| 7,294,752 B1 | 11/2007 | Propp |
| 7,316,672 B1 | 1/2008 | Hunt et al. |
| D565,177 S | 3/2008 | Locke et al. |
| 7,338,482 B2 | 3/2008 | Lockwood et al. |
| 7,351,250 B2 | 4/2008 | Zamierowski |

(56) References Cited

U.S. PATENT DOCUMENTS

| | | |
|---|---|---|
| 7,361,184 B2 | 4/2008 | Joshi |
| 7,381,211 B2 | 6/2008 | Zamierowski |
| 7,381,859 B2 | 6/2008 | Hunt et al. |
| 7,396,345 B2 | 7/2008 | Knighton et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,438,705 B2 | 10/2008 | Karpowicz et al. |
| 7,494,482 B2 | 2/2009 | Orgill et al. |
| 7,524,315 B2 * | 4/2009 | Blott ............... A61M 1/0058 604/317 |
| 7,534,240 B1 | 5/2009 | Johnson |
| 7,534,927 B2 | 5/2009 | Lockwood |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,645,253 B2 | 1/2010 | Gura et al. |
| 7,645,269 B2 | 1/2010 | Zamierowski |
| 7,670,323 B2 | 3/2010 | Hunt et al. |
| 7,699,823 B2 | 4/2010 | Haggstrom et al. |
| 7,699,830 B2 | 4/2010 | Martin |
| 7,708,724 B2 | 5/2010 | Weston |
| 7,717,313 B2 | 5/2010 | Criscuolo et al. |
| 7,722,582 B2 | 5/2010 | Lina et al. |
| 7,731,702 B2 | 6/2010 | Bybordi et al. |
| 7,749,531 B2 | 7/2010 | Booher |
| 7,753,894 B2 | 7/2010 | Blott et al. |
| 7,759,537 B2 | 7/2010 | Convatec |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. et al. |
| 7,790,946 B2 | 9/2010 | Mulligan |
| 7,794,438 B2 | 9/2010 | Henley et al. |
| 7,794,450 B2 | 9/2010 | Blott et al. |
| 7,811,269 B2 | 10/2010 | Boynton et al. |
| 7,815,616 B2 | 10/2010 | Boehringer et al. |
| 7,825,289 B2 | 11/2010 | Vess |
| 7,828,782 B2 | 11/2010 | Suzuki |
| 7,838,717 B2 | 11/2010 | Haggstrom et al. |
| 7,838,723 B1 | 11/2010 | Schmidt et al. |
| 7,846,141 B2 | 12/2010 | Weston |
| 7,862,339 B2 | 1/2011 | Mulligan |
| 7,883,494 B2 | 2/2011 | Martin |
| 7,909,805 B2 | 3/2011 | Weston |
| 7,910,791 B2 | 3/2011 | Coffey |
| 7,922,703 B2 | 4/2011 | Riesinger |
| 7,927,318 B2 | 4/2011 | Risk, Jr. et al. |
| 7,942,866 B2 | 5/2011 | Radl et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,021,347 B2 | 9/2011 | Vitaris et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,092,441 B2 | 1/2012 | Sugito |
| 8,100,887 B2 | 1/2012 | Weston et al. |
| 8,105,295 B2 | 1/2012 | Blott et al. |
| 8,118,794 B2 | 2/2012 | Weston et al. |
| 8,128,615 B2 | 3/2012 | Blott et al. |
| 8,152,785 B2 | 4/2012 | Vitaris |
| 8,162,907 B2 | 4/2012 | Heagle |
| 8,162,909 B2 | 4/2012 | Blott et al. |
| 8,207,392 B2 | 6/2012 | Haggstrom et al. |
| 8,235,955 B2 | 8/2012 | Blott et al. |
| 8,235,972 B2 | 8/2012 | Adahan |
| 8,241,261 B2 | 8/2012 | Randolph et al. |
| 8,251,979 B2 | 8/2012 | Malhi |
| 8,257,326 B2 | 9/2012 | Vitaris |
| 8,257,327 B2 | 9/2012 | Blott et al. |
| 8,257,328 B2 | 9/2012 | Augustine et al. |
| 8,267,908 B2 | 9/2012 | Coulthard |
| 8,282,611 B2 | 10/2012 | Weston |
| 8,298,200 B2 | 10/2012 | Vess et al. |
| 8,303,552 B2 | 11/2012 | Weston |
| 8,372,050 B2 | 2/2013 | Jaeb et al. |
| 8,382,731 B2 | 2/2013 | Johannison |
| 8,398,614 B2 | 3/2013 | Blott et al. |
| 8,409,157 B2 | 4/2013 | Haggstrom et al. |
| 8,425,478 B2 | 4/2013 | Olson |
| 8,444,612 B2 | 5/2013 | Patel et al. |
| 8,449,509 B2 | 5/2013 | Weston |
| 8,460,255 B2 | 6/2013 | Joshi et al. |
| 8,545,464 B2 | 10/2013 | Weston |
| 8,545,466 B2 | 10/2013 | Andresen et al. |
| 8,568,386 B2 | 10/2013 | Malhi |
| 8,569,566 B2 | 10/2013 | Blott et al. |
| 8,628,505 B2 | 1/2014 | Weston |
| 8,641,691 B2 | 2/2014 | Fink et al. |
| 8,663,198 B2 | 3/2014 | Buan et al. |
| 8,715,256 B2 | 5/2014 | Greener |
| 8,764,732 B2 | 7/2014 | Hartwell |
| 8,795,243 B2 | 8/2014 | Weston |
| 8,808,274 B2 | 8/2014 | Hartwell |
| 8,829,263 B2 | 9/2014 | Haggstrom et al. |
| 8,834,451 B2 | 9/2014 | Haggstrom et al. |
| 8,956,336 B2 | 2/2015 | Haggstrom et al. |
| 9,061,095 B2 | 6/2015 | Adie et al. |
| 9,127,665 B2 | 9/2015 | Locke et al. |
| 9,168,330 B2 | 10/2015 | Joshi et al. |
| 9,198,801 B2 | 12/2015 | Weston |
| 9,199,012 B2 | 12/2015 | Vitaris et al. |
| 9,211,365 B2 | 12/2015 | Weston |
| 9,220,822 B2 | 12/2015 | Hartwell et al. |
| 9,283,118 B2 | 3/2016 | Locke et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,446,178 B2 | 9/2016 | Blott et al. |
| 9,452,248 B2 | 9/2016 | Blott et al. |
| 2001/0000795 A1 | 5/2001 | Bolian, II et al. |
| 2001/0016985 A1 | 8/2001 | Insley et al. |
| 2001/0018308 A1 | 8/2001 | Quick et al. |
| 2001/0018602 A1 | 8/2001 | Augustine et al. |
| 2001/0027302 A1 | 10/2001 | Glaug et al. |
| 2001/0027305 A1 | 10/2001 | Raidel et al. |
| 2001/0029956 A1 | 10/2001 | Argenta |
| 2001/0031943 A1 | 10/2001 | Urie |
| 2001/0034499 A1 | 10/2001 | Sessions et al. |
| 2001/0043943 A1 | 11/2001 | Coffey |
| 2001/0044610 A1 | 11/2001 | Kim et al. |
| 2001/0051178 A1 | 12/2001 | Blatchford et al. |
| 2001/0053904 A1 | 12/2001 | Abuto |
| 2002/0007167 A1 | 1/2002 | Dan et al. |
| 2002/0007169 A1 | 1/2002 | Graef et al. |
| 2002/0016577 A1 | 2/2002 | Ohmstede |
| 2002/0019602 A1 | 2/2002 | Geng |
| 2002/0019614 A1 | 2/2002 | Woon et al. |
| 2002/0026166 A1 | 2/2002 | Graef et al. |
| 2002/0034914 A1 | 3/2002 | De Leon et al. |
| 2002/0035352 A1 | 3/2002 | Ronnberg et al. |
| 2002/0035354 A1 | 3/2002 | Mirle et al. |
| 2002/0062113 A1 | 5/2002 | Thomas et al. |
| 2002/0064639 A1 | 5/2002 | Rearick et al. |
| 2002/0065494 A1 | 5/2002 | Lockwood et al. |
| 2002/0087136 A1 | 7/2002 | Widlund |
| 2002/0090511 A1 | 7/2002 | Smith et al. |
| 2002/0110672 A1 | 8/2002 | Muratore-Pallatino et al. |
| 2002/0115952 A1 * | 8/2002 | Johnson ............... A61M 1/0088 602/41 |
| 2002/0115954 A1 | 8/2002 | Worthley |
| 2002/0123728 A1 | 9/2002 | Graef et al. |
| 2002/0133132 A1 | 9/2002 | Copat et al. |
| 2002/0143286 A1 | 10/2002 | Tumey |

(56) References Cited

U.S. PATENT DOCUMENTS

| | | |
|---|---|---|
| 2002/0143312 A1 | 10/2002 | Graeme, III et al. |
| 2002/0150678 A1 | 10/2002 | Cramer et al. |
| 2002/0151836 A1 | 10/2002 | Burden |
| 2002/0161346 A1 | 10/2002 | Lockwood et al. |
| 2002/0165509 A1 | 11/2002 | Baer et al. |
| 2002/0169054 A1 | 11/2002 | Roberts |
| 2002/0176964 A1 | 11/2002 | Koslow |
| 2002/0177831 A1 | 11/2002 | Daley et al. |
| 2002/0180092 A1 | 12/2002 | Abba et al. |
| 2002/0183704 A1 | 12/2002 | Fields et al. |
| 2003/0009122 A1 | 1/2003 | Veras |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0045707 A1 | 3/2003 | West et al. |
| 2003/0045825 A1 | 3/2003 | Etheredge, III |
| 2003/0050617 A1 | 3/2003 | Chen et al. |
| 2003/0065292 A1 | 4/2003 | Darouiche |
| 2003/0069563 A1 | 4/2003 | Johnson |
| 2003/0070780 A1 | 4/2003 | Chen et al. |
| 2003/0073967 A1 | 4/2003 | Wahlstrom et al. |
| 2003/0078532 A1 | 4/2003 | Ruszczak et al. |
| 2003/0088202 A1 | 5/2003 | Gilman |
| 2003/0088229 A1 | 5/2003 | Baker et al. |
| 2003/0088231 A1 | 5/2003 | Yoshimasa et al. |
| 2003/0093041 A1 | 5/2003 | Risk, Jr. et al. |
| 2003/0093044 A1 | 5/2003 | Wahlstrom et al. |
| 2003/0097086 A1 | 5/2003 | Gura |
| 2003/0097101 A1 | 5/2003 | Schmidt et al. |
| 2003/0097105 A1 | 5/2003 | Chen et al. |
| 2003/0097113 A1 | 5/2003 | Molee |
| 2003/0105442 A1 | 6/2003 | Johnston et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0124311 A1 | 7/2003 | Cree et al. |
| 2003/0125649 A1 | 7/2003 | Mcintosh et al. |
| 2003/0134559 A1 | 7/2003 | Delzer et al. |
| 2003/0135174 A1 | 7/2003 | Benecke et al. |
| 2003/0135177 A1 | 7/2003 | Baker |
| 2003/0139696 A1 | 7/2003 | Boukanov et al. |
| 2003/0144619 A1 | 7/2003 | Augustine |
| 2003/0150551 A1 | 8/2003 | Baker |
| 2003/0157857 A1 | 8/2003 | Cook et al. |
| 2003/0171675 A1 | 9/2003 | Rosenberg |
| 2003/0171729 A1 | 9/2003 | Kaun et al. |
| 2003/0175798 A1 | 9/2003 | Raees et al. |
| 2003/0180341 A1 | 9/2003 | Gooch et al. |
| 2003/0199800 A1 | 10/2003 | Levin |
| 2003/0208149 A1 | 11/2003 | Coffey |
| 2003/0208175 A1 | 11/2003 | Gross et al. |
| 2003/0212357 A1 | 11/2003 | Pace |
| 2003/0212359 A1 | 11/2003 | Butler |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2003/0225383 A1 | 12/2003 | Glaug et al. |
| 2004/0006319 A1 | 1/2004 | Lina et al. |
| 2004/0019338 A1 | 1/2004 | Litvay et al. |
| 2004/0019339 A1 | 1/2004 | Ranganathan et al. |
| 2004/0019340 A1 | 1/2004 | McBride |
| 2004/0019342 A1 | 1/2004 | Nagasuna et al. |
| 2004/0024375 A1 | 2/2004 | Litvay |
| 2004/0030304 A1 | 2/2004 | Hunt et al. |
| 2004/0033750 A1 | 2/2004 | Everett et al. |
| 2004/0039391 A1 | 2/2004 | Argenta et al. |
| 2004/0039415 A1 | 2/2004 | Zamierowski |
| 2004/0049146 A1 | 3/2004 | Kolte et al. |
| 2004/0050254 A1 | 3/2004 | Tanaka et al. |
| 2004/0054338 A1 | 3/2004 | Byordi |
| 2004/0054343 A1 | 3/2004 | Barnett et al. |
| 2004/0054344 A1 | 3/2004 | Roettger et al. |
| 2004/0057855 A1 | 3/2004 | Gerlach et al. |
| 2004/0064111 A1 | 4/2004 | Lockwood et al. |
| 2004/0064132 A1 | 4/2004 | Boehringer |
| 2004/0065420 A1 | 4/2004 | Graef et al. |
| 2004/0078011 A1 | 4/2004 | Stevens |
| 2004/0078016 A1 | 4/2004 | Baker |
| 2004/0082925 A1 | 4/2004 | Patel |
| 2004/0087884 A1 | 5/2004 | Haddock et al. |
| 2004/0087918 A1 | 5/2004 | Johnson et al. |
| 2004/0087927 A1 | 5/2004 | Suzuki |
| 2004/0093026 A1 | 5/2004 | Weidenhagen et al. |
| 2004/0102752 A1 | 5/2004 | Chen et al. |
| 2004/0106888 A1 | 6/2004 | Lutri et al. |
| 2004/0111074 A1 | 6/2004 | Eliasson |
| 2004/0116551 A1 | 6/2004 | Terry |
| 2004/0122383 A1 | 6/2004 | Romano et al. |
| 2004/0122434 A1 | 6/2004 | Argenta et al. |
| 2004/0138602 A1 | 7/2004 | Rossen |
| 2004/0162512 A1 | 8/2004 | Liedtke et al. |
| 2004/0167456 A1 | 8/2004 | Kingsford et al. |
| 2004/0167482 A1* | 8/2004 | Watson ............... A61M 1/0001 604/317 |
| 2004/0177935 A1 | 9/2004 | Hamed et al. |
| 2004/0181199 A1 | 9/2004 | Moberg-Alehammar et al. |
| 2004/0193218 A1 | 9/2004 | Butler |
| 2004/0204696 A1 | 10/2004 | Chen |
| 2004/0220505 A1 | 11/2004 | Worthley |
| 2004/0225208 A1 | 11/2004 | Johnson |
| 2004/0230173 A1 | 11/2004 | Barge et al. |
| 2004/0230184 A1 | 11/2004 | Babusik et al. |
| 2004/0241213 A1 | 12/2004 | Bray |
| 2004/0241214 A1 | 12/2004 | Kirkwood et al. |
| 2004/0243042 A1 | 12/2004 | Lipman |
| 2004/0243073 A1 | 12/2004 | Lockwood et al. |
| 2004/0243080 A1 | 12/2004 | Baer |
| 2004/0243081 A1 | 12/2004 | Suzuki et al. |
| 2004/0249353 A1 | 12/2004 | Risk, Jr. et al. |
| 2004/0253894 A1 | 12/2004 | Fell et al. |
| 2004/0254552 A1 | 12/2004 | Mangold |
| 2004/0260230 A1 | 12/2004 | Randolph |
| 2005/0004534 A1 | 1/2005 | Lockwood et al. |
| 2005/0008825 A1 | 1/2005 | Casey et al. |
| 2005/0010153 A1 | 1/2005 | Lockwood et al. |
| 2005/0012616 A1 | 1/2005 | Forster et al. |
| 2005/0013992 A1 | 1/2005 | Azad et al. |
| 2005/0015036 A1 | 1/2005 | Lutri et al. |
| 2005/0020955 A1 | 1/2005 | Sanders et al. |
| 2005/0049566 A1 | 3/2005 | Vukos et al. |
| 2005/0058694 A1 | 3/2005 | Nielsen |
| 2005/0070835 A1 | 3/2005 | Joshi |
| 2005/0070858 A1 | 3/2005 | Lockwood et al. |
| 2005/0079361 A1 | 4/2005 | Hamed et al. |
| 2005/0080372 A1 | 4/2005 | Nielsen et al. |
| 2005/0085795 A1 | 4/2005 | Lockwood et al. |
| 2005/0090787 A1 | 4/2005 | Risk, Jr. et al. |
| 2005/0096616 A1 | 5/2005 | Arora et al. |
| 2005/0107732 A1 | 5/2005 | Boyde |
| 2005/0112979 A1 | 5/2005 | Sawyer et al. |
| 2005/0119631 A1 | 6/2005 | Giloh et al. |
| 2005/0119737 A1 | 6/2005 | Bene et al. |
| 2005/0119739 A1* | 6/2005 | Glazier ............... A61F 2/1613 623/6.13 |
| 2005/0131327 A1* | 6/2005 | Lockwood .......... A61M 1/0058 602/41 |
| 2005/0136773 A1 | 6/2005 | Yahiaoui et al. |
| 2005/0137539 A1 | 6/2005 | Biggie et al. |
| 2005/0147562 A1 | 7/2005 | Hunter et al. |
| 2005/0165371 A1 | 7/2005 | Giacometti |
| 2005/0177190 A1 | 8/2005 | Zamierowski |
| 2005/0182445 A1 | 8/2005 | Zamierowski |
| 2005/0203471 A1 | 9/2005 | Kelly |
| 2005/0215965 A1 | 9/2005 | Schmidt et al. |
| 2005/0215967 A1 | 9/2005 | Toro et al. |
| 2005/0222527 A1 | 10/2005 | Miller et al. |
| 2005/0222547 A1 | 10/2005 | Beruda et al. |
| 2005/0228353 A1 | 10/2005 | Thomas |
| 2005/0261642 A1* | 11/2005 | Weston ............... A61M 1/0088 604/313 |
| 2005/0261643 A1 | 11/2005 | Byordi et al. |
| 2005/0261649 A1 | 11/2005 | Cohen |

(56) References Cited

U.S. PATENT DOCUMENTS

| | | |
|---|---|---|
| 2005/0267429 A1 | 12/2005 | Cohen |
| 2006/0003604 A1 | 1/2006 | Angerpointner |
| 2006/0009744 A1 | 1/2006 | Erdman et al. |
| 2006/0015087 A1 | 1/2006 | Risk, Jr. et al. |
| 2006/0020234 A1 | 1/2006 | Chou et al. |
| 2006/0020250 A1 | 1/2006 | Chester et al. |
| 2006/0029650 A1 | 2/2006 | Coffey |
| 2006/0039742 A1 | 2/2006 | Cable, Jr. et al. |
| 2006/0040579 A1 | 2/2006 | Sheldon |
| 2006/0041247 A1 | 2/2006 | Petrosenko et al. |
| 2006/0058750 A1 | 3/2006 | Di Girolamo et al. |
| 2006/0069365 A1 | 3/2006 | Sperl et al. |
| 2006/0069366 A1 | 3/2006 | Cole |
| 2006/0069367 A1 | 3/2006 | Waksmundzki et al. |
| 2006/0069375 A1 | 3/2006 | Waksmundzki et al. |
| 2006/0079852 A1 | 4/2006 | Bubb et al. |
| 2006/0094997 A1 | 5/2006 | Kurata |
| 2006/0100586 A1 | 5/2006 | Karpowicz et al. |
| 2006/0100594 A1 | 5/2006 | Adams et al. |
| 2006/0107642 A1 | 5/2006 | Smith et al. |
| 2006/0116620 A1 | 6/2006 | Oyaski |
| 2006/0122548 A1 | 6/2006 | Abrams |
| 2006/0122572 A1 | 6/2006 | Suarez |
| 2006/0129080 A1 | 6/2006 | Bjornberg et al. |
| 2006/0149170 A1 | 7/2006 | Boynton et al. |
| 2006/0153904 A1 | 7/2006 | Smith et al. |
| 2006/0161122 A1 | 7/2006 | Erdman et al. |
| 2006/0178650 A1 | 8/2006 | Hakannsson et al. |
| 2006/0184147 A1 | 8/2006 | Hamed |
| 2006/0206047 A1 | 9/2006 | Lampe et al. |
| 2006/0206073 A1 | 9/2006 | Crane et al. |
| 2006/0206074 A1 | 9/2006 | Bernal et al. |
| 2006/0282028 A1 | 12/2006 | Howard et al. |
| 2007/0003606 A1 | 1/2007 | Booher |
| 2007/0005028 A1 | 1/2007 | Risk, Jr. et al. |
| 2007/0010797 A1 | 1/2007 | Nishtala et al. |
| 2007/0014837 A1 | 1/2007 | Johnson et al. |
| 2007/0016152 A1 | 1/2007 | Karpowicz |
| 2007/0021697 A1 | 1/2007 | Ginther et al. |
| 2007/0167926 A1 | 1/2007 | Blott et al. |
| 2007/0027414 A1* | 2/2007 | Hoffman .......... A61M 1/0088 602/2 |
| 2007/0027433 A1 | 2/2007 | Garcia et al. |
| 2007/0032754 A1 | 2/2007 | Walsh |
| 2007/0032755 A1 | 2/2007 | Walsh |
| 2007/0032778 A1 | 2/2007 | Heaton et al. |
| 2007/0040454 A1 | 2/2007 | Freudenberger et al. |
| 2007/0049859 A1 | 3/2007 | Propp |
| 2007/0055205 A1 | 3/2007 | Wright et al. |
| 2007/0055209 A1* | 3/2007 | Patel .......... A61F 13/00063 604/315 |
| 2007/0060848 A1 | 3/2007 | Erdmann |
| 2007/0060892 A1 | 3/2007 | Propp |
| 2007/0066945 A1 | 3/2007 | Martin |
| 2007/0073254 A1 | 3/2007 | Ponomarenko et al. |
| 2007/0078467 A1 | 4/2007 | Mullen |
| 2007/0100308 A1 | 5/2007 | Miyairi |
| 2007/0156104 A1 | 7/2007 | Lockwood et al. |
| 2007/0161937 A1 | 7/2007 | Aali |
| 2007/0167096 A1 | 7/2007 | Scott |
| 2007/0167884 A1 | 7/2007 | Mangrum et al. |
| 2007/0179460 A1 | 8/2007 | Adahan |
| 2007/0185426 A1 | 8/2007 | Ambrosio et al. |
| 2007/0185463 A1 | 8/2007 | Mulligan |
| 2007/0203442 A1 | 8/2007 | Bechert et al. |
| 2007/0219532 A1 | 9/2007 | Karpowicz et al. |
| 2007/0224903 A1 | 9/2007 | Chakravarty et al. |
| 2007/0225663 A1 | 9/2007 | Watt et al. |
| 2007/0244451 A1 | 10/2007 | Romano et al. |
| 2007/0254550 A1 | 11/2007 | Hamed et al. |
| 2007/0265586 A1 | 11/2007 | Joshi et al. |
| 2007/0270070 A1 | 11/2007 | Hamed |
| 2007/0282236 A1 | 12/2007 | LaGreca |
| 2008/0004549 A1 | 1/2008 | Anderson et al. |
| 2008/0004559 A1 | 1/2008 | Riesinger |
| 2008/0004581 A1 | 1/2008 | Babusik et al. |
| 2008/0015532 A1 | 1/2008 | Waksmundzki |
| 2008/0031748 A1 | 2/2008 | Ihle et al. |
| 2008/0039759 A1 | 2/2008 | Holm et al. |
| 2008/0051716 A1 | 2/2008 | Stutz |
| 2008/0058691 A1 | 3/2008 | Sorensen |
| 2008/0071234 A1 | 3/2008 | Kelch et al. |
| 2008/0071235 A1 | 3/2008 | Locke et al. |
| 2008/0082075 A1 | 4/2008 | Morrell-Schwartz |
| 2008/0090050 A1 | 4/2008 | Seyler et al. |
| 2008/0108977 A1 | 5/2008 | Heaton et al. |
| 2008/0114317 A1 | 5/2008 | Seyler |
| 2008/0119586 A1 | 5/2008 | Byerly et al. |
| 2008/0119802 A1 | 5/2008 | Reisinger |
| 2008/0132821 A1 | 6/2008 | Propp et al. |
| 2008/0132855 A1 | 6/2008 | Romano et al. |
| 2008/0147024 A1 | 6/2008 | Potts et al. |
| 2008/0167592 A1 | 7/2008 | Greer |
| 2008/0167593 A1 | 7/2008 | Flesichmann |
| 2008/0183119 A1 | 7/2008 | Joshi |
| 2008/0188820 A1 | 8/2008 | Joshi |
| 2008/0195017 A1 | 8/2008 | Robinson et al. |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0223378 A1 | 9/2008 | Henderson et al. |
| 2008/0234616 A1 | 9/2008 | Shives et al. |
| 2008/0234641 A1 | 9/2008 | Locke et al. |
| 2008/0243100 A1 | 10/2008 | Wu et al. |
| 2008/0255533 A1 | 10/2008 | Wu et al. |
| 2008/0275409 A1 | 11/2008 | Kane et al. |
| 2008/0281281 A1 | 11/2008 | Meyer et al. |
| 2008/0306407 A1 | 12/2008 | Taylor |
| 2008/0306456 A1 | 12/2008 | Riesinger |
| 2008/0312621 A1 | 12/2008 | Hundorf et al. |
| 2008/0312622 A1 | 12/2008 | Hundorf et al. |
| 2009/0005746 A1 | 1/2009 | Nielsen et al. |
| 2009/0012484 A1 | 1/2009 | Nielsen et al. |
| 2009/0036873 A1 | 2/2009 | Nielsen et al. |
| 2009/0054855 A1 | 2/2009 | Blott et al. |
| 2009/0054856 A1 | 2/2009 | Mormino et al. |
| 2009/0062760 A1 | 3/2009 | Wright et al. |
| 2009/0069759 A1 | 3/2009 | Blott et al. |
| 2009/0076472 A1 | 3/2009 | Goldwasser et al. |
| 2009/0112175 A1 | 4/2009 | Bissah et al. |
| 2009/0125004 A1 | 5/2009 | Shen et al. |
| 2009/0131888 A1 | 5/2009 | Joshi |
| 2009/0137973 A1 | 5/2009 | Karpowicz et al. |
| 2009/0157024 A1 | 6/2009 | Song |
| 2009/0177135 A1 | 7/2009 | Rogers et al. |
| 2009/0192499 A1 | 7/2009 | Weston et al. |
| 2009/0198201 A1 | 8/2009 | Adahan |
| 2009/0204085 A1 | 8/2009 | Biggie et al. |
| 2009/0204087 A1 | 8/2009 | Herfert et al. |
| 2009/0216168 A1 | 8/2009 | Eckstein et al. |
| 2009/0216170 A1 | 8/2009 | Robinson et al. |
| 2009/0221977 A1 | 9/2009 | Blott et al. |
| 2009/0221990 A1 | 9/2009 | Jaeb et al. |
| 2009/0227935 A1 | 9/2009 | Zanella et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254053 A1 | 10/2009 | Svensby et al. |
| 2009/0254054 A1 | 10/2009 | Blott et al. |
| 2009/0264837 A1 | 10/2009 | Adahan |
| 2009/0270820 A1 | 10/2009 | Johnson |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299341 A1 | 12/2009 | Kazala et al. |
| 2009/0299342 A1 | 12/2009 | Cavanaugh, II et al. |
| 2009/0306580 A1 | 12/2009 | Blott et al. |
| 2009/0312723 A1 | 12/2009 | Blott et al. |

(56) References Cited

U.S. PATENT DOCUMENTS

| | | |
|---|---|---|
| 2010/0010458 A1 | 1/2010 | Sherman |
| 2010/0010461 A1 | 1/2010 | Herfert et al. |
| 2010/0030171 A1 | 2/2010 | Canada et al. |
| 2010/0036334 A1 | 2/2010 | Heagle et al. |
| 2010/0036342 A1 | 2/2010 | Carlucci et al. |
| 2010/0036367 A1 | 2/2010 | Krohn |
| 2010/0042074 A1 | 2/2010 | Weston |
| 2010/0048072 A1 | 2/2010 | Kauscheke et al. |
| 2010/0055158 A1 | 3/2010 | Vitaris et al. |
| 2010/0063483 A1 | 3/2010 | Adahan |
| 2010/0063484 A1 | 3/2010 | Heagle |
| 2010/0069858 A1 | 3/2010 | Olson |
| 2010/0069863 A1 | 3/2010 | Olson |
| 2010/0087767 A1 | 4/2010 | McNeil |
| 2010/0100062 A1 | 4/2010 | Christensen |
| 2010/0100075 A1 | 4/2010 | Weston |
| 2010/0106114 A1 | 4/2010 | Weston et al. |
| 2010/0106120 A1 | 4/2010 | Holm |
| 2010/0106121 A1 | 4/2010 | Holm |
| 2010/0121286 A1 | 5/2010 | Locke et al. |
| 2010/0121298 A1 | 5/2010 | Seyler et al. |
| 2010/0122417 A1 | 5/2010 | Vrzalik et al. |
| 2010/0125258 A1 | 5/2010 | Coulthard et al. |
| 2010/0150991 A1 | 6/2010 | Bernstein |
| 2010/0160881 A1 | 6/2010 | Lin et al. |
| 2010/0168695 A1 | 7/2010 | Robles et al. |
| 2010/0191196 A1 | 7/2010 | Heagle |
| 2010/0191198 A1 | 7/2010 | Heagle |
| 2010/0198161 A1 | 8/2010 | Propp |
| 2010/0207768 A1 | 8/2010 | Pidgeon |
| 2010/0210986 A1 | 8/2010 | Sanders |
| 2010/0217177 A1 | 8/2010 | Cali et al. |
| 2010/0249733 A9 | 9/2010 | Blott |
| 2010/0256545 A1 | 10/2010 | Aali et al. |
| 2010/0256584 A1 | 10/2010 | Litvay |
| 2010/0256586 A1 | 10/2010 | Bergstrom et al. |
| 2010/0262090 A1 | 10/2010 | Riesinger |
| 2010/0262091 A1 | 10/2010 | Larsson |
| 2010/0268198 A1 | 10/2010 | Buan et al. |
| 2010/0274207 A1 | 10/2010 | Weston |
| 2010/0278518 A1 | 11/2010 | Gordon |
| 2010/0298866 A1 | 11/2010 | Fischvogt |
| 2010/0305490 A1 | 12/2010 | Coulthard et al. |
| 2010/0305526 A1 | 12/2010 | Robinson et al. |
| 2010/0318043 A1 | 12/2010 | Malhi |
| 2010/0318047 A1 | 12/2010 | Ducker et al. |
| 2010/0318052 A1 | 12/2010 | Ha et al. |
| 2010/0324510 A1 | 12/2010 | Andresen et al. |
| 2010/0324516 A1 | 12/2010 | Braga et al. |
| 2011/0004172 A1 | 1/2011 | Eckstein et al. |
| 2011/0009835 A1 | 1/2011 | Blott |
| 2011/0015557 A1 | 1/2011 | Aali et al. |
| 2011/0015593 A1 | 1/2011 | Svedman et al. |
| 2011/0028921 A1 | 2/2011 | Hartwell et al. |
| 2011/0034892 A1 | 2/2011 | Buan |
| 2011/0052664 A1 | 3/2011 | Tennican et al. |
| 2011/0054422 A1 | 3/2011 | Locke et al. |
| 2011/0054423 A1 | 3/2011 | Blott et al. |
| 2011/0059329 A1 | 3/2011 | Dobrawa et al. |
| 2011/0060303 A1 | 3/2011 | Bissah et al. |
| 2011/0092927 A1 | 4/2011 | Wilkes et al. |
| 2011/0092958 A1 | 4/2011 | Jacobs |
| 2011/0098621 A1 | 4/2011 | Fabo et al. |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0125119 A1 | 5/2011 | Weismantel et al. |
| 2011/0130712 A1 | 6/2011 | Topaz |
| 2011/0137222 A1 | 6/2011 | Masini |
| 2011/0152813 A1 | 6/2011 | Ellingson |
| 2011/0172616 A1 | 7/2011 | Hartwell et al. |
| 2011/0178375 A1 | 7/2011 | Forster |
| 2011/0183109 A1 | 7/2011 | Seyler et al. |
| 2011/0184364 A1 | 7/2011 | Biggs et al. |
| 2011/0184370 A1 | 7/2011 | Seyler et al. |
| 2011/0208145 A1 | 8/2011 | Zhang et al. |
| 2011/0213286 A1 | 9/2011 | Riesinger |
| 2011/0218509 A1 | 9/2011 | Dontas |
| 2011/0223413 A1 | 9/2011 | Herfert et al. |
| 2011/0224631 A1 | 9/2011 | Simmons |
| 2011/0230849 A1 | 9/2011 | Coulthard |
| 2011/0238026 A1 | 9/2011 | Zhang et al. |
| 2011/0245788 A1 | 10/2011 | Canada |
| 2011/0247636 A1 | 10/2011 | Pollack |
| 2011/0257572 A1 | 10/2011 | Locke et al. |
| 2011/0264175 A1 | 10/2011 | Barsky et al. |
| 2011/0268932 A1 | 11/2011 | Catalan et al. |
| 2011/0282309 A1 | 11/2011 | Adie et al. |
| 2011/0251567 A1 | 12/2011 | Blott et al. |
| 2012/0004632 A1 | 1/2012 | Zhang et al. |
| 2012/0016322 A1 | 1/2012 | Coulthard et al. |
| 2012/0041399 A1 | 2/2012 | Blott et al. |
| 2012/0041403 A1 | 2/2012 | Bennett et al. |
| 2012/0045639 A1 | 2/2012 | Whitmore et al. |
| 2012/0053538 A1 | 3/2012 | Blott et al. |
| 2012/0053547 A1 | 3/2012 | Schroeder et al. |
| 2012/0065664 A1 | 3/2012 | Avitable et al. |
| 2012/0071848 A1 | 3/2012 | Zhang et al. |
| 2012/0095380 A1 | 4/2012 | Gergeley et al. |
| 2012/0095426 A1 | 4/2012 | Visscher et al. |
| 2012/0101465 A1 | 4/2012 | Mcguire, Jr. |
| 2012/0116334 A1 | 5/2012 | Albert et al. |
| 2012/0123311 A1 | 5/2012 | Weidemann et al. |
| 2012/0136325 A1 | 5/2012 | Allen |
| 2012/0136329 A1 | 5/2012 | Carney |
| 2012/0143158 A1 | 6/2012 | Yang et al. |
| 2012/0157942 A1 | 6/2012 | Weston |
| 2012/0172778 A1 | 7/2012 | Rastegar et al. |
| 2012/0197229 A1 | 8/2012 | Buan |
| 2012/0203145 A1 | 8/2012 | Nilsson |
| 2012/0203189 A1 | 8/2012 | Barta et al. |
| 2012/0220968 A1 | 8/2012 | Confalone et al. |
| 2012/0232502 A1 | 9/2012 | Lowing |
| 2012/0238932 A1 | 9/2012 | Atteia et al. |
| 2012/0302440 A1 | 11/2012 | Theliander et al. |
| 2012/0308780 A1 | 12/2012 | Rottger et al. |
| 2012/0310186 A1 | 12/2012 | Moghe et al. |
| 2012/0310197 A1 | 12/2012 | Thomas |
| 2012/0330253 A1 | 12/2012 | Robinson et al. |
| 2013/0012902 A1 | 1/2013 | Rovaniemi |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0110058 A1 | 5/2013 | Adie et al. |
| 2013/0116635 A1 | 5/2013 | Fleischmann |
| 2013/0138054 A1 | 5/2013 | Fleischmann |
| 2013/0144230 A1 | 6/2013 | Wu et al. |
| 2013/0150814 A1 | 6/2013 | Buan |
| 2013/0165878 A1 | 6/2013 | Heagle |
| 2013/0267921 A1 | 10/2013 | Weston |
| 2013/0274688 A1 | 10/2013 | Weston |
| 2013/0331822 A1 | 12/2013 | Patel |
| 2014/0018753 A1 | 1/2014 | Joshi et al. |
| 2014/0114263 A1 | 4/2014 | Weston |
| 2014/0114268 A1 | 4/2014 | Auguste et al. |
| 2014/0228791 A1 | 8/2014 | Hartwell |
| 2014/0236109 A1 | 8/2014 | Greener |
| 2014/0249493 A1 | 9/2014 | Hartwell |
| 2014/0316359 A1 | 10/2014 | Collinson et al. |
| 2015/0032035 A1 | 1/2015 | Banwell et al. |
| 2015/0209492 A1 | 7/2015 | Blott et al. |
| 2015/0308994 A1 | 10/2015 | Hammond et al. |
| 2016/0051737 A1 | 2/2016 | Joshi et al. |
| 2016/0144084 A1 | 5/2016 | Collinson et al. |
| 2016/0298620 A1 | 10/2016 | Cordoba et al. |
| 2016/0317357 A1 | 11/2016 | Vitaris et al. |
| 2017/0095598 A1 | 4/2017 | Joshi et al. |

FOREIGN PATENT DOCUMENTS

| | | |
|---|---|---|
| CA | 2 390 513 | 5/2001 |
| CA | 2 121 688 | 7/2001 |
| CA | 2 408 305 | 11/2001 |

(56) References Cited

FOREIGN PATENT DOCUMENTS

| | | |
|---|---|---|
| CA | 2 458 285 | 3/2003 |
| CA | 2 157 772 | 9/2003 |
| DE | 28 09 828 | 9/1978 |
| DE | 34 43 101 | 5/1986 |
| DE | 3 935 818 | 5/1991 |
| DE | 4 012 232 | 10/1991 |
| DE | 90 17 289 | 6/1992 |
| DE | 41 11 122 A1 | 4/1993 |
| DE | 295 04 378 U1 | 10/1995 |
| DE | 198 44 355 | 4/2000 |
| DE | 20 2004 017 052 | 7/2005 |
| DE | 20 2004 018 245 | 7/2005 |
| DE | 20 2005 019 670 | 4/2006 |
| EP | 0 053936 | 6/1982 |
| EP | 0 257 916 | 3/1988 |
| EP | 0 340 018 | 11/1989 |
| EP | 0 355 186 | 2/1990 |
| EP | 0 358 302 | 3/1990 |
| EP | 0 541 251 | 5/1993 |
| EP | 0 549 781 | 9/1996 |
| EP | 0 748 894 | 12/1996 |
| EP | 0 853 950 | 7/1998 |
| EP | 0 777 504 | 10/1998 |
| EP | 0 875 224 | 11/1998 |
| EP | 0 782 421 | 7/1999 |
| EP | 0 941 726 | 9/1999 |
| EP | 1 013 290 | 6/2000 |
| EP | 1 048 278 | 11/2000 |
| EP | 1 066 809 | 1/2001 |
| EP | 1 088 569 | 4/2001 |
| EP | 1 139 951 | 10/2001 |
| EP | 1 219 311 | 7/2002 |
| EP | 1 897 569 | 8/2002 |
| EP | 0 708 620 | 5/2003 |
| EP | 1 312 328 | 5/2003 |
| EP | 1 088 569 | 8/2003 |
| EP | 1 452 156 | 9/2004 |
| EP | 1 476 217 | 11/2004 |
| EP | 1 440 667 | 3/2006 |
| EP | 1 284 777 | 4/2006 |
| EP | 1 755 701 | 2/2007 |
| EP | 1 171 065 | 3/2007 |
| EP | 1 476 217 | 3/2008 |
| EP | 1 955 887 | 8/2008 |
| EP | 1 121 163 | 11/2008 |
| EP | 2 098 257 | 9/2009 |
| EP | 2 161 011 | 3/2010 |
| EP | 2 263 627 | 12/2010 |
| EP | 2 021 046 | 3/2012 |
| EP | 2 462 908 | 6/2012 |
| EP | 2 259 767 | 12/2012 |
| EP | 2 547 375 | 1/2013 |
| EP | 2 596 815 | 5/2013 |
| EP | 2 305 325 | 4/2014 |
| EP | 2 687 245 | 9/2014 |
| EP | 2 544 642 | 1/2015 |
| EP | 2 648 668 | 1/2015 |
| EP | 3 072 542 | 9/2016 |
| FR | 1163907 | 10/1958 |
| FR | 2 939 320 | 6/2010 |
| GB | 114 754 | 4/1918 |
| GB | 641061 | 8/1950 |
| GB | 1224009 | 3/1971 |
| GB | 1 255 395 | 12/1971 |
| GB | 1 549 756 | 8/1979 |
| GB | 1549756 | 8/1979 |
| GB | 2099306 | 12/1982 |
| GB | 2 235 877 A | 3/1991 |
| GB | 2 307 180 | 5/1997 |
| GB | 2 195 255 A | 4/1998 |
| GB | 2 329 127 A | 3/1999 |
| GB | 2 336 546 A | 10/1999 |
| GB | 2 344 531 A | 6/2000 |
| GB | 2 355 228 | 4/2001 |
| GB | 2 378 392 | 2/2003 |
| GB | 2 415 908 | 1/2006 |
| GB | 2 435 422 A | 8/2007 |
| GB | 2 435 423 A | 8/2007 |
| GB | 2 489 947 | 10/2012 |
| JP | 2003-165843 | 6/2003 |
| JP | 2006-084129 | 3/2006 |
| SU | 1251912 A1 | 4/1983 |
| SU | 1762940 | 1/1989 |
| WO | WO 1980/01139 | 6/1980 |
| WO | WO 1980/02182 | 10/1980 |
| WO | WO 1983/00742 | 3/1983 |
| WO | WO 1984/01904 | 5/1984 |
| WO | WO 1989/05133 | 6/1989 |
| WO | WO 1990/11795 | 10/1990 |
| WO | WO 1991/00718 | 1/1991 |
| WO | WO 1991/11161 | 8/1991 |
| WO | WO 1991/11162 | 8/1991 |
| WO | WO 1992/19313 | 11/1992 |
| WO | WO 1992/20299 | 11/1992 |
| WO | WO 1993/01778 | 2/1993 |
| WO | WO 1993/01779 | 2/1993 |
| WO | WO 1993/01780 | 2/1993 |
| WO | WO 1993/01781 | 2/1993 |
| WO | WO 1993/009727 | 5/1993 |
| WO | WO 1993/09745 | 5/1993 |
| WO | WO 1993/11726 | 6/1993 |
| WO | WO 1994/20041 | 9/1994 |
| WO | WO 1994/23677 | 10/1994 |
| WO | WO 1995/04511 | 2/1995 |
| WO | WO 1995/13042 | 5/1995 |
| WO | WO 1995/13776 | 5/1995 |
| WO | WO 1995/13779 | 5/1995 |
| WO | WO 1995/14451 | 6/1995 |
| WO | WO 1995/16424 | 6/1995 |
| WO | WO 1995/29959 | 11/1995 |
| WO | WO 1996/05873 | 2/1996 |
| WO | WO 1996/07783 | 3/1996 |
| WO | WO 1996/21410 | 7/1996 |
| WO | WO 1997/11658 | 4/1997 |
| WO | WO 1997/14384 | 4/1997 |
| WO | WO 1998/20916 | 5/1998 |
| WO | WO 1998/22279 | 5/1998 |
| WO | WO 1999/01173 | 1/1999 |
| WO | WO 1999/04830 | 2/1999 |
| WO | WO 1999/39671 | 8/1999 |
| WO | WO 1999/45876 | 9/1999 |
| WO | WO 1999/45878 | 9/1999 |
| WO | WO 1999/56687 | 11/1999 |
| WO | WO 2000/00016 | 1/2000 |
| WO | WO 2000/00127 | 1/2000 |
| WO | WO 2000/00129 | 1/2000 |
| WO | WO 2000/00130 | 1/2000 |
| WO | WO 2000/00131 | 1/2000 |
| WO | WO 2000/07653 | 2/2000 |
| WO | WO 2000/21586 | 4/2000 |
| WO | WO 2000/40190 | 7/2000 |
| WO | WO 2000/42957 | 7/2000 |
| WO | WO 2000/50143 | 8/2000 |
| WO | WO 2000/59424 | 10/2000 |
| WO | WO 2000/59438 | 10/2000 |
| WO | WO 2001/19430 | 3/2001 |
| WO | WO 2001/34223 | 5/2001 |
| WO | WO 2001/37922 | 5/2001 |
| WO | WO 2001/072251 | 10/2001 |
| WO | WO 2001/85248 | 11/2001 |
| WO | WO 2001/89431 | 11/2001 |
| WO | WO 2001/90465 | 11/2001 |
| WO | WO 2001/93793 | 12/2001 |
| WO | WO 2002/017840 | 3/2002 |
| WO | WO 2002/24132 | 3/2002 |
| WO | WO 2002/26180 | 4/2002 |
| WO | WO 2002/38096 | 5/2002 |
| WO | WO 2002/076379 | 10/2002 |
| WO | WO 2002/083046 | 10/2002 |
| WO | WO 2012/143665 | 10/2002 |
| WO | WO 2002/092783 | 11/2002 |
| WO | WO 2003/005943 | 1/2003 |
| WO | WO 2003/018098 | 3/2003 |
| WO | WO 2003/030966 | 4/2003 |

(56) References Cited

FOREIGN PATENT DOCUMENTS

| | | |
|---|---|---|
| WO | WO 2003/045492 | 6/2003 |
| WO | WO 2003/057070 | 7/2003 |
| WO | WO 2003/057071 | 7/2003 |
| WO | WO 2003/057307 | 7/2003 |
| WO | WO 2003/073971 | 9/2003 |
| WO | WO 2003/086232 | 10/2003 |
| WO | WO 2003/092620 | 11/2003 |
| WO | WO 2003/101508 | 12/2003 |
| WO | WO 2004/018020 | 3/2004 |
| WO | WO 2004/024300 | 3/2004 |
| WO | WO 2004/037334 | 5/2004 |
| WO | WO 2004/043321 | 5/2004 |
| WO | WO 2004/073566 | 9/2004 |
| WO | WO 2004/077387 | 9/2004 |
| WO | WO 2004/098474 | 11/2004 |
| WO | WO 2005/009488 | 2/2005 |
| WO | WO 2005/025447 | 3/2005 |
| WO | WO 2005/025666 | 3/2005 |
| WO | WO 2005/051461 | 6/2005 |
| WO | WO 2005/070480 | 8/2005 |
| WO | WO 2005/082435 | 9/2005 |
| WO | WO 2005/115497 | 12/2005 |
| WO | WO 2005/123170 | 12/2005 |
| WO | WO 2006/002417 | 1/2006 |
| WO | WO 2006/052839 | 5/2006 |
| WO | WO 2006/056294 | 6/2006 |
| WO | WO 2006/105305 | 10/2006 |
| WO | WO 2006/105892 | 10/2006 |
| WO | WO 2007/024230 | 3/2007 |
| WO | WO 2007/030598 | 3/2007 |
| WO | WO 2007/030601 | 3/2007 |
| WO | WO 2007/035038 | 3/2007 |
| WO | WO 2007/040606 | 4/2007 |
| WO | WO 2007/077214 | 7/2007 |
| WO | WO 2007/077216 | 7/2007 |
| WO | WO 2007/116347 | 10/2007 |
| WO | WO 2007/133644 | 11/2007 |
| WO | WO 2008/049277 | 5/2008 |
| WO | WO 2008/131895 | 11/2008 |
| WO | WO 2009/146441 | 3/2009 |
| WO | WO 2009/066105 | 5/2009 |
| WO | WO 2009/066106 | 5/2009 |
| WO | WO 2009/071929 | 6/2009 |
| WO | WO 2009/071935 | 6/2009 |
| WO | WO 2009/124100 | 10/2009 |
| WO | WO 2009/126103 | 10/2009 |
| WO | WO 2009/152021 | 12/2009 |
| WO | WO 2009/158128 | 12/2009 |
| WO | WO 2010/032951 | 3/2010 |
| WO | WO 2010/082872 | 7/2010 |
| WO | WO 2010/089448 | 8/2010 |
| WO | WO 2010/139926 | 12/2010 |
| WO | WO 2010/142959 | 12/2010 |
| WO | WO 2011/023650 | 3/2011 |
| WO | WO 2011/058311 | 5/2011 |
| WO | WO 2011/080427 | 7/2011 |
| WO | WO 2011/113728 | 9/2011 |
| WO | WO 2011/115908 | 9/2011 |
| WO | WO 2011/128651 | 10/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/152368 | 12/2011 |
| WO | WO 2012/009370 | 1/2012 |
| WO | WO 2012/022484 | 2/2012 |
| WO | WO 2012/035787 | 3/2012 |
| WO | WO 2012/074512 | 6/2012 |
| WO | WO 2012/041296 | 8/2012 |
| WO | WO 2012/131237 | 10/2012 |
| WO | WO 2012/140378 | 10/2012 |
| WO | WO 2012/146656 | 11/2012 |
| WO | WO 2012/150235 | 11/2012 |
| WO | WO 2012/168298 | 12/2012 |
| WO | WO 2013/010907 | 1/2013 |
| WO | WO 2013/014317 | 1/2013 |
| WO | WO 2013/029652 | 3/2013 |
| WO | WO 2013/060732 | 5/2013 |
| WO | WO 2013/083800 | 6/2013 |
| WO | WO 2013/090810 | 6/2013 |
| WO | WO 2013/149078 | 10/2013 |
| WO | WO 2013/136181 | 11/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/108476 | 7/2014 |
| WO | WO 2014/113253 | 7/2014 |
| WO | WO 2015/022334 | 2/2015 |
| WO | WO 2015/022340 | 2/2015 |
| WO | WO 2015/031216 | 3/2015 |
| ZA | 9605526 | 2/1997 |

OTHER PUBLICATIONS

US 6,306,115, 10/2001, Kelly et al. (withdrawn)
US 7,186,244, 03/2007, Hunt et al. (withdrawn)
Arnljots, et al., "Irrigation Treatment in Split-thickness Skin Grafting of Intractable Leg Ulcers," Scand J Plast Reconstr Surg 19: 211-213,1985.
Gorica Zivadinovic, et al., "Vacuum Therapy in the Treatment of Peripheral Blood Vessels," Conference Papers of the 5th Timok Medical Days, Majdanpek, 1986 (161-164).
Sandén, Göran MD., et al., "Staphylococcal Wound Infection in the Pig: Part II. Inoculation, Quantification of Bacteria, and Reproducibility," Annals of Plastic Surgery, vol. 23, No. 3, Sep. 1989, (219-223).
Davydov, Y. et al., "Bacteriological and Cytological Assessment of Vacuum Therapy of Purulent Wounds", Vestnik Khirurgii, Oct. 1988 (48-52).
Davydov, Y. et al., "Concepts for Clinical Biological Management of the Wound Process in the Treatment of Purulent Wounds Using Vacuum Therapy," Vestnik Khirugii, Feb. 1991, 132-135).
Davydov, Y. et al., "Vacuum Therapy in the Treatment of Purulent Lactation Mastitis," Russian Journal: Vesnik Khirurgii, Sep. 1986 (66-70).
Davydov, Y. et al., "Vacuum Therapy in treatment of Acute Purulent Diseases of Soft Tissues and Purulent Wounds," Vestnik Khirurgii, (Surgeon's Herald), Medicine Publishers, 1986.
Membrane Filters, in 16 pages, from website: http://www.advantecmfs.com/catalog/filt/membrane.pdf#page=11 (date unknown, but believed to be copyright 2001-2011).
Brochure for the Boehringer Engenex, 33 pages, Aug. 2007.
Chardack, et al., "Experimental studies on Synthetic Substitutes for Skin and Their Use in the Treatment of Burns," vol. 155, No. 1 (128-136), 1961.
Fleischmann, "Vacuum Sealing for Treatment of Problematical Wounds", University Surgical Clinic and Polyclinic—Accident Surgery Department, WundForum Spezial-IHW 94.
Greer, et al., Techniques for Applying Subatmospheric Pressure Dressing to Wounds in Difficult Regions of Anatomy, JWOCN, vol. 26, No. 5, 1999 pp. 250-253.
KCI, Inc., Basic Application Guide for V.A.C. Dressings for Wounds Without Exposed Vessels, Organs, Tendons and Nerves, 2008, in 2 pages.
Kostiuchenok, et al., "The Vacuum Effect in the Surgical Treatment of Purulent Wounds," Russian Journal: Vestnik Khirurgii, Sep. 1986 (18-21).
Meyer, MD., et al., "In Surgery, Medicine and the Specialties A Manual of its Practical Application", Bier's Hyperemic Treatment, Second Revised Edition, W.B. Saunders Company, 1909.
Morcos, Anthony C.; Voice Coil Actuators & Their Use in Advanced Motion Control Systems; Motion; Jul./Aug. 1995; pp. 25-27.
Mulder, GD, et al., "Clinicians' Pocket Guide to Chronic Wound Repair," Wound Healing Publications Second Edition, 1991.
Pentair Pool Products, 2000 Series Stainless Steel D. E. Filters (2006).

(56) References Cited

OTHER PUBLICATIONS

Ryosuke Fujimoro, MD., et al., "Sponge Fixation Method for Treatment of Early Scars," From the Department of Dermatology in the Faculty Medicine, Kyoto University, vol. 42, No. 4, Oct. 1968 (322-326).
Smith, S.R.G., et al.: "Surgical drainage," British Journal of Hospital Medicine, Jun. 1985.
Stoll, "Energetic Remedies—Cupping: Healing Within a Vacuum," https:I/www.suite101.com/article.cfm/ energetic)remedies/74531, Apr. 13, 2005.
Svedman, et al., "Staphylococcal Wound Infection in the Pig: Part I. Course," Annals of Plastic Surgery, vol. 23, No. 3, Sep. 1989 (212-218).
Takakura, Hikaru et al.: Bio-Filter: Allergen Inactivating Filter Coated with Hyperthermostable Protease, 21 (1 0) Bio Ind 7-13 (2004).
Usupov, et al., "Active Wound Drainage," Russian Journal: Vestnik Khirugii, Apr. 1987 (42-45).
Van Way, C.W., "Prevention of suction-induced gastric mucosal damage in dogs," Crital Care Medicine, vol. 15, No. 8, pp. 774-777, 1987.
Worth, M.H., et al.: "The effectiveness of Bacterial Filtration in Vented Wound Drains," Journal of Surgical Research, 17, 405-407, 1979.
U.S. Appl. No. 10/599,720, filed Oct. 6, 2006, Blott et al.
U.S. Appl. No. 12/192,000, filed Apr. 14, 2008, Hartwell et al.
Argenta, Louis C., et al., "Vacuum Assisted Closure: A New Method for Wound Control and Treatment; Clinical Experience", Ann Plas Surg 1997;38:563-577 (Dec. 10, 1996).
Aubrey, D.A., et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Biblehimer, Helen L., "Dealing With a Wound that Drains 1.5 Liters a Day," RN, Aug. 1986, pp. 21-23, USA.
Bier, A., Hyperemia as a Therapeutic Agent, Ed. Dr. Gustavus M. Blech, A. Robertson & Co., Chicago 1905.
Brubacher, Lynda L., "To Heal a Draining Wound", RN, Mar. 1982, pp. 30-35, USA.
Bucalo et al. "Inhibition of Cell Proliferation by Chronic Wound Fluid." Wound Repair and Regeneration. Miami, 1993. pp. 181-186.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chintamani, et al., "Half versus full vacuum suction drainage after modified radical mastectomy for breast cancer—a prospective randomized clinical trial", Research Article (Jan. 27, 2005), 1-5.
Costunchenok, B.M., et al., Effect of Vacuum on Surgical Purulent Wounds, Vestnik Chirurgia 1986, Sep. 18-20 (in Russian with English translation).
Davydov et al. "Pathogenic Mechanism of the Effect of Vacuum Therapy on the Course of the Wound Process" pp. 43-46 (Dec. 1990).
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y. , et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Fleischmann, et al., Vacuum Sealing: Indication, Technique and Results, Emr J Orthop Surg Tramatol (1995) 5:37-40.
Fleischmann, W. Wund Forum Spezial, "Vakuumversiegelung zur Behandlung von Problemwunden" (with English translation: Vacuum Sealing for Treatment of Problematical Wounds), IHW '94, 6 pages.
Garcia-Rinaldi, R., et al., Improving the Efficiency of Wound Drainage Catheters, Amer. Journ. of Surg., Sep. 1975, 130, 372-373.
Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
Jeter, Katherine F., et al., "Managing Draining Wounds and Fistulae: New and Established Methods", Chronic Wound Care, 1990, pp. 240-246.
Johnson, F.E., An Improved Technique for Skin Graft Placement using a Suction Drain, Surgery, Gynecology & Obstetrics, Dec. 1984, 159(6), 584-585.
KCI, Inc., If It's Not V.A.C. Therapy, It's Not Negative Pressure Wound Therapy, KCI Brochure, Jan. 2005, 1-5.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum-Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Landes, R.R. and I. Melnick, An Improved Suction Device for Draining Wounds, Arch. Surg., May 1972, 104, p. 707.
Linden van der, Willem, Randomized Trial of Drainage After Cholecystectomy, Modern Operative Techniques, Voluje 141, Feb. 1981, pgs. 289-294.
McFarlane, R. M., "The Use of Continuous Suction Under Skin Flaps", F.R.C.S.(c), vol. 1, pp. 77-86 (1958).
McLaughlan, James, Sterile Microenvironment for Postoperative Wound Care, The Lancet, pp. 503-504, Sep. 2, 1978.
Meyer, Weight-Loaded Syringes as a Simple and Cheap Alternative to Pumps for Vacuum-Enhanced Wound Healing, Plastic and Reconstructive Srug., Jun. 2005, 2174-2176 (Correspondence).
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Nakayama, Y., et al., "A New Method for the Dressing of Free Skin Grafts", Plastic and Reconstructive Surgery, Dec. 1990 pp. 1216-1219, UK.
Nursing75, Wound Suction: Better Drainage with Fewer Problems, Nursing, vol. 5, No. 10, Oct. 1975, pp. 52-55.
Ramirez, O.M., et al., Optimal Wound Healing under Op-Site Dressing, Ideas and Innovations, 73(3), pp. 474-475.
Ranson, John H. M.D., Safer Intraperitoneal Sump Drainage, Surgery Gynnecology and Obstetrics, pp. 841-842, 1973 vol. 137.
Sames, C.P., Sealing of Wounds with Vacuum Drainage, Br. Med. Journ., Nov. 5, 1977, p. 1223, Correspondence.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).
Svedman, "A Dressing Allowing Continuous Treatment of a Biosurface," IRCS Medical Science: Biomedical Technology; Clinical Medicine; Surgery and Transplantation, 7, 221 (1979).

(56) References Cited

OTHER PUBLICATIONS

Svedman, "A Dressing System Providing Fluid Supply and Suction Drainage Used for Continuous or Intermittent Irrigation," Annals of Plastic Surgery, vol. 17, No. 2, Aug. 1986 (125-133).
Svedman, "Irrigation Treatment of Leg Ulcers," The Lancet, Sep. 3, 1983 (532-534).
Svedman, P., "Irrigation Treatment in Split-Thickness Skin Grafting of Intractable Leg Ulcers," Scand J. Plast. Reconst. Surg., 19:211-213, 1985.
Swift, et al, "Quorum Sensing in Aeromonas hydrophila and Aeromonas salmoncida: Identification of LuxRI Homologs AhyRI and AsaRI and Their Cognate N-Acylhomoserine Lactone Signal Molecules," J. Bacteriol., 179(17):5271-5281 (1997).
Teder and Svedman et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Vijanto, J. and J. Raekallio, Local Hyperalimentation of Open Wounds, Br. J. surg., 1976, 63, 427-430.
Wackenfors, A., et al., Effects of Vacuum-Assisted Closure Therapy on Inguinal Wound Edge Microvascular Blood Flow, Wound Rep. Reg, 2004, 12, 600-606.
Webb, New Techniques in Wound Management: Vacuum-Assisted Wound Closure, Journal of the American Academy of Orthopadic Surgeons, v. 10, No. 5, pp. 303-311, Sep. 2002.
Webster's Revised Unabridged Dictionary, published 1913 by C. & G. Merriam Co., definition of Flapper Valve, downloaded from Free Online Dictionary.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
Wu, W.S., et al. Vacuum therapy as an intermediate phase in wound closure: a clinical experience, Eur J Past Surg (2000) 23: 174-177.
Communication of Notice of Opposition dated Jul. 23, 2014, Opposition of European patent EP 2021047 B1, dated Jul. 16, 2014, on behalf of Sorbion GmbH & Co.KG, and cited publications D1-D25, in 568 pages. EP 2021047 B1 is related to the present application by virtue of a common priority claim to U.S. Appl. No. 11/432,855, now U.S. Pat. No. 7,615,036 [with references as noted within opposition].
English translation of Opposition of European patent EP 2021047 B1, dated Jul. 16, 2014, on behalf of Sorbion GmbH & Co., in 32 pages. EP 2021047 B1 is related to the present application by virtue of a common priority claim to U.S. Appl. No. 11/432,855, now U.S. Pat. No. 7,615,036.
Kendall ULTEC Hydrocolloid Dressing (4"×4"), product ordering page, web page downloaded Jul. 13, 2014.
Protz, Kerstin: "Modern Wundauflagen unterstutzen Heilungsprozess", Wundversorgung: Indikation und Anwendung, Geriatrie Journal Apr. 2005, pp. 3333-3339.
U.S. Appl. No. 15/413,132, filed Jan. 23, 2017, Buan.
"Technology Watch", May 1989, in 1 page.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.

\* cited by examiner

SELF CONTAINED WOUND DRESSING WITH MICROPUMP

CROSS-REFERENCE TO RELATED APPLICATIONS

This application is a continuation of U.S. patent application Ser. No. 13/483,109, filed on May 30, 2012, now U.S. Pat. No. 8,829,263, which is a continuation of U.S. patent application Ser. No. 12/917,103, filed Nov. 1, 2010, now U.S. Pat. No. 8,207,392, which is a divisional of U.S. patent application Ser. No. 12/496,263, filed Jul. 1, 2009, now U.S. Pat. No. 7,838,717, which is a continuation of U.S. patent application Ser. No. 11/517,210, filed on Sep. 6, 2006, now U.S. Pat. No. 7,569,742, which claims priority to U.S. Provisional Patent Application No. 60/714,812 filed on Sep. 7, 2005, entitled "SELF CONTAINED WOUND DRESSING WITH MICROPUMP." The disclosure of each of these prior applications is incorporated by reference in its entirety.

BACKGROUND

1. Technical Field

The present disclosure relates to an apparatus for treating an open wound, and, more specifically, relates to a self contained wound dressing with a micropump system which draws wound fluids into a vacuum zone of the dressing to facilitate the wound healing process.

2. Description of Related Art

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Wound dressings have been used in the medical industry to protect and/or facilitate healing of open wounds. One technique has been to use negative pressure therapy, which is also known as suction or vacuum therapy. A variety of negative pressure devices have been developed to allow excess wound fluids, i.e., exudates to be removed while at the same time isolating the wound to protect the wound and, consequently, affect recovery time. Various wound dressings have been modified to promote the healing of open wounds.

Issues that continually need to be addressed when using a wound dressing include ease of use, efficiency of healing a wound, and a source of constant negative pressure. Thus, there remains a need to constantly improve negative pressure wound dressings for open wounds.

SUMMARY

In one preferred embodiment, a wound dressing apparatus includes a wound dressing member dimensioned for positioning relative to a wound bed and a micropump system. The micropump system includes a micropump for applying subatmospheric pressure to at least the wound dressing member to facilitate removal of fluid from the wound bed. The micropump is preferably mounted relative to the wound dressing member. The preferred micropump is adapted to produce subatmospheric pressure ranging between about 20 mmHg and about 500 mmHg.

The micropump system may include control means to control operation of the micropump. The micropump system may further include a pressure sensor adapted to detect pressure at a predetermined location relative to the wound dressing member, and send a corresponding signal to the control means. The control means may include a motor controller adapted to control or vary the output of the micropump in response to the pressure sensed by the pressure sensor. The micropump system may also include a power source, e.g., a battery, for actuating the micropump. The battery may be adapted for implantation within the wound dressing member or external to the wound dressing member. Rechargeable batteries are envisioned.

The preferred wound dressing member includes a lower member positionable adjacent the wound bed, an upper absorbent member positionable adjacent the lower member, and a top member. The micropump is at least partially positioned within the upper absorbent member. The top member is an adhesive member which is adapted to be secured about the wound bed or wound bed perimeter to provide a seal between the wound dressing member and tissue surrounding the wound bed. The lower member may include at least one of a medicament, an anti-infective agent, an antimicrobial, polyhexamethylene biguanide (hereinafter, "PHMB"), antibiotics, analgesics, healing factors, vitamins, growth factors, and nutrients and/or one of a microbead packing and/or absorbent foam. The upper absorbent member may comprise a material selected from the group consisting of foams, nonwoven composite fabrics, cellulose fabrics, super absorbent polymers, and combinations thereof.

The top member may include an occlusive material which may or may not be transparent. The wound dressing member includes a visual pressure indicator for indicating a level of pressure within the wound dressing member. The wound dressing member may include a saturation indicator to identify a degree of saturation of the wound dressing member. The top member includes an access door associated therewith and being selectively movable between a closed position substantially enclosing the wound dressing member and an open position permitting internal access to the wound dressing member.

In another embodiment, the wound dressing apparatus includes a wound dressing member including an absorbent member positionable relative to a wound bed and a micropump system contained within the wound dressing member. The micropump system includes a micropump for applying subatmospheric pressure to the wound bed to facilitate removal of fluid from the wound bed and an implantable or attachable power source for supplying power to the micropump. The micropump system includes control means to control operation of the micropump and a pressure sensor to detect pressure at a predetermined location relative to the wound dressing member.

BRIEF DESCRIPTION OF THE DRAWINGS

Various embodiments of the subject wound dressing are described herein with reference to the drawings wherein.

DESCRIPTION OF THE PREFERRED EMBODIMENTS

The composite wound dressing apparatus of the present disclosure promotes healing of a wound via the use of a micropump system housed within a wound dressing. The micropump system includes a miniature pump that applies a subatmospheric pressure to the wound to effectively draw wound fluid or exudate away from the wound bed without the need for an external vacuum source. Hence, the wound dressing apparatus in the form of wound dressing and micropump system is portable which allows the patient mobility that is unavailable when an external vacuum source is used. The patient does not need to be restricted for any period of time while exudate is being removed from the wound.

Figure 1:
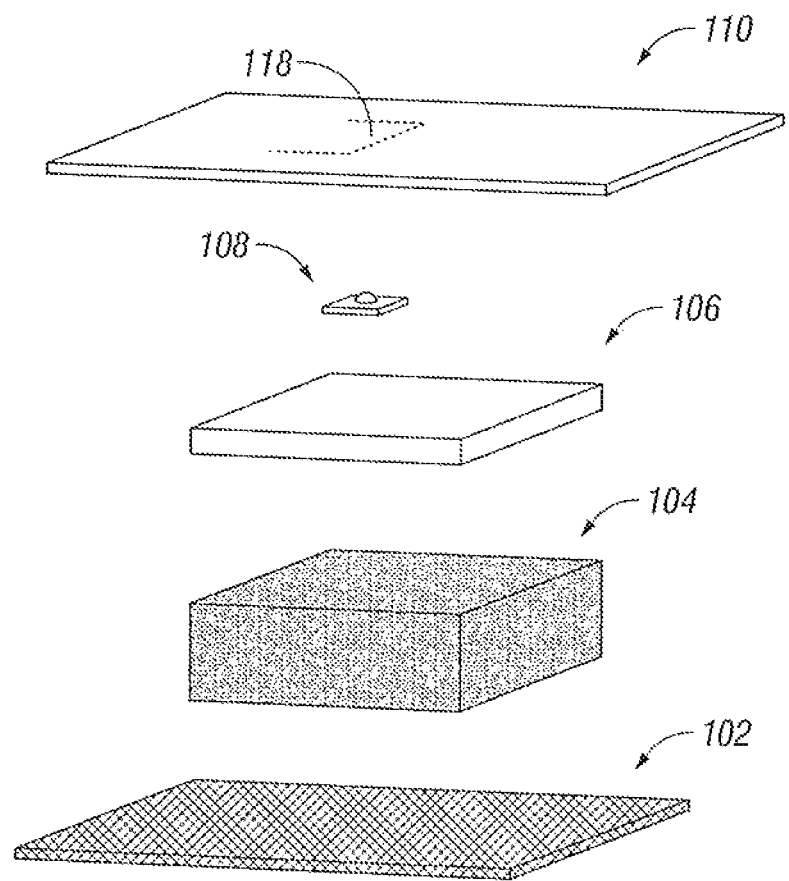
FIG. 1 is a perspective view of a self contained wound dressing and micropump system in accordance with the principles of the present disclosure.
Figure 2:
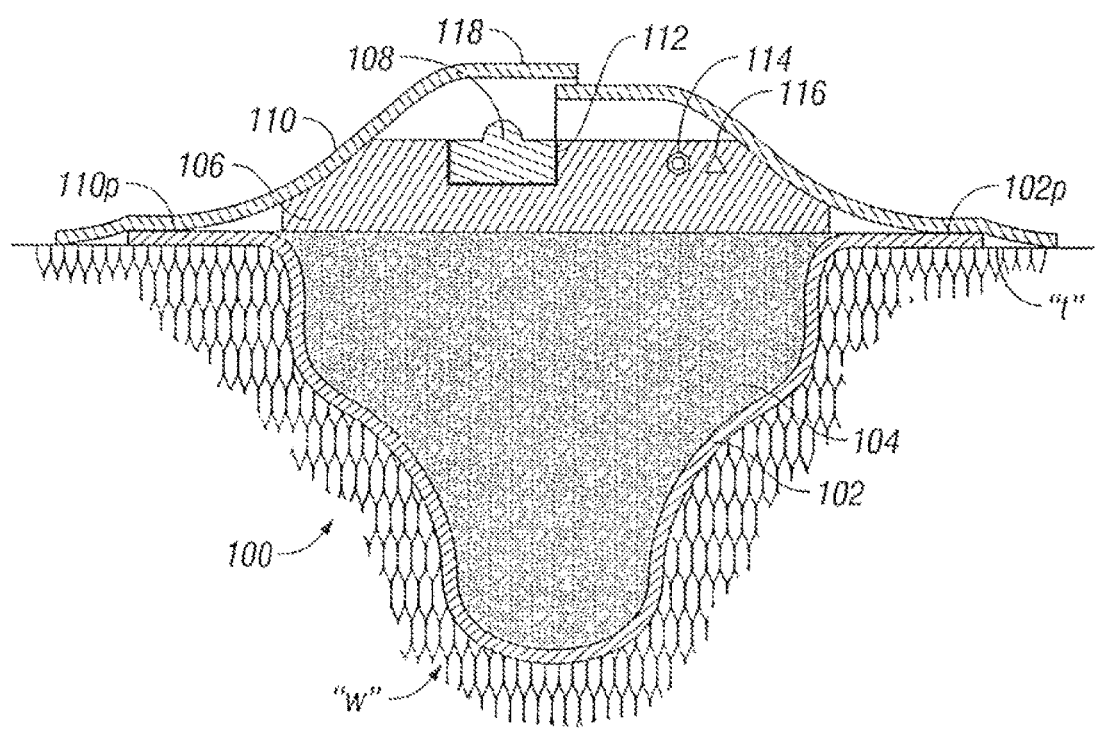
FIG. 2 is a side cross-sectional view illustrating the wound dressing on a wound bed and in a normal expanded condition in the absence of a vacuum.

Referring now to FIGS. 1 and 2, the composite wound dressing apparatus 10 in accordance with a preferred embodiment of the present disclosure is illustrated in the form of a wound dressing 100 with multiple layers arranged in juxtaposed or superposed relation. The multiple layers include, but are not limited to a base, or lower layer 102, a packing layer 104, an absorbent layer 106 which houses a micropump system 108, and a occlusive adherent top layer 110.

The base layer 102 is in direct contact with the wound bed "w" and may be adherent to the tissue or non-adherent. The base layer 102 is typically porous. "Non-adherent" as used herein refers to a material that does not adhere to tissues in and around the wound bed. "Porous" as used herein refers to a material which contains numerous small perforations or pores which allow wound fluids of all kinds to pass through the material to the dressing layers above. The passage of wound fluid through the non-adherent material is preferably unidirectional such that wound exudate does not flow back to the wound bed. This direction flow feature could be in the form of directional apertures imparted into the material layer, a lamination of materials of different absorption to the base layer 102 or specific material selection that encourages directional flow. Bidirectional flow materials are also contemplated for base layer 102 to permit infusion of fluids medicants into the wound. Exemplary materials used as the base layer 102 include a contact layer sold under the trademark XEROFLO™ by Kendall Corp, a division of TycoHealthcare.

In addition, agents such as hydrogels and medicaments could be bonded or coated to the base layer 102 to reduce bioburden in the wound, promote healing and reduce pain associated with dressing changes or removal. Medicaments include, for example, antimicrobial agents, growth factors, antibiotics, analgesics, debridement agents, and the like. Furthermore, when an analgesic is used, the analgesic could include a mechanism that would allow the release of that agent prior to dressing removal or change.

The layer proximal to the base layer 102 is the packing layer 104. The packing layer 104 is intended to absorb and capture wound fluid and exudates. Exemplary materials used as the packing layer 104 include the antimicrobial dressing sold under the trademark KERLIX™ by Kendall Corp., a division of TycoHealthcare. Those skilled in the art will recognize that the packing layer 104 can be formed into any suitable shape. One preferred characteristic as to shape is that the packing layer 104 is suitable to conform to a particular shape of the wound.

A further use for the packing layer 104 is to decrease the incidence of infection in the wound bed. Hence, the packing layer 104 may be treated with medicaments. Medicaments include, for example, an anti-infective agent such as an antiseptic or other suitable antimicrobial or combination of antimicrobials, polyhexamethylene biguanide (hereinafter, "PHMB"), antibiotics, analgesics, debridement agents, healing factors such as vitamins, growth factors, nutrients and the like, as well as a simple flushing with agents such as isotonic saline solution.

The layer proximal to the packing layer 104 is the absorbent layer 106. The absorbent layer 106 of the wound dressing apparatus 10 is intended to absorb and capture wound fluid and exudates. The absorbent layer 106 also houses the micropump system 108. Preferably, the absorbent layer 106 is preformed or shaped to accept the micropump system 108. In this regard, the absorbent layer 106 may have a concavity or recess 112 to accommodate the micropump system 108. Alternatively, the absorbent layer 106 may be pliable so as to be shaped or formed to receive and/or confine the micropump system 108. Exemplary absorbent materials include foams, nonwoven composite fabrics, cellulosic fabrics, super absorbent polymers, and combinations thereof. Preferably, the absorbent layer 106 can absorb a substantial volume of exudates, e.g., up to at least 100 cubic centimeters (cc) or more of wound fluid. The absorbent layer 106 may include multiple layers.

The absorbent layer 106 also may be treated with medicaments. Medicaments include, for example, an anti-infective agent such as an antiseptic or other suitable antimicrobial or combination of antimicrobials, polyhexamethylene biguanide, antibiotics, analgesics, healing factors such as vitamins, debridement agents, growth factors, nutrients and the like, as well as a flushing agents such as isotonic saline solution.

The absorbent layer 106 may further include a pressure indicator 114 independent from the micropump system 108. The pressure indicator 114 may be mounted to, secured to, or embedded within the absorbent layer 106 or within the confines of wound dressing apparatus 10. Alternatively, the pressure indicator 114 is external to the wound dressing 100 and communicates with the interior of the wound dressing through a pressure tube or the like. The pressure indicator 114 may be in the form of the commercially available pressure sensor sold under the tradename Dynamic IP® Pressure Sensors by PCB® Piezotronics. The pressure indicator 114 may be color coded where one color on the device (e.g., red) indicates a non vacuum state and a second color (e.g., green) indicates a suitable vacuum state. The absorbent layer 106 may further include a saturation indicator 116 mounted to, or embedded within, the surface of the absorbent layer 106. The saturation indicator 116 may be a litmus paper such as but not limited to PEHANAL® and PAN-PEHA® which indicates to the user of the level or degree of saturation of the absorbent layer 106 with exudates and wound fluids. The saturation indicator 116 will assist the user in determining the remaining capacity of the absorbent layer 106, or if the absorbent layer 106 needs replacing. Although disclosed as being mounted to or embedded within absorbent layer 106, the saturation indicator 116 may be positioned within any component of wound dressing 100.

With reference still to FIGS. 1 and 2, the adherent top layer 110 encompasses the perimeter of the wound dressing 100 to surround the wound bed "w" to provide a seal around the perimeter of the wound bed "w". For instance, the sealing mechanism may be any adhesive bonded to a layer that surrounds the wound bed "w". The adhesive must provide acceptable adhesion to the tissue "t" surrounding the wound bed "w" skin, e.g., the periwound area, and be acceptable for use on skin without contact deterioration (for example, the adhesive should preferably be non-irritating and non-sensitizing.) The adhesive may be permeable to permit the contacted skin to breathe and transmit moisture. Additionally, the adhesive could be activated or de-activated by an external stimulus such as heat or a given fluid solution or chemical reaction. Adhesives include, for example, Ultec® Hydrocolloid Dressing or Curagel® Hydrogel by Kendall Corp., a division of Tyco Healthcare Group LP.

The adherent top layer 110 is preferably in the form of a sheet mounted proximal to the absorbent layer 106. Preferably, the top layer 110 is not bonded to the absorbent layer 106 to allow for easy replacement of the absorbent layer 106. In a preferred embodiment, the peripheral portions 110P of the top layer 110 are bonded to the periphery 102P of the base layer 102 and secured to the tissue "t" about the wound bed "w". It is anticipated that removable liners may also be used to protect the adhesive surface of the adherent layer 110 prior to use.

The top layer 110 is typically a flexible material, e.g., resilient or elastomeric, that seals the top of the wound dressing 100. An exemplary flexible material includes the fully or partially transparent dressing manufactured under the trademark Polyskin® II by Kendall Corp, a division of Tyco Healthcare Group LP. Polyskin® II is a transparent, semi-permeable material which permits passage of moisture from the wound site, and provides a barrier to microbes and fluid containment. In the alternative, the top layer 110 may be impermeable to moisture. The transparency of the top layer 110 provides visual indicia of the status of the wound dressing and more particularly, the status of the saturation level of the layers of the wound dressing. More specifically, the transparency of the top layer 110 permits the clinician to view the respective statuses of the pressure indicator 114 and the saturation indicator 116.

The top layer 110 may include an access door 118 to provide access to the interior of the wound dressing 100 and/or the wound bed "w". The door 118 could be a flap integrally formed with the top layer 110 or a separate component connected to the top layer 110 via a hinge or the like. The door 118 is preferably resealable to maintain the integrity of the wound dressing 100 and to provide a seal relative to the top layer 110. One suitable means for releasably sealing the door 118 includes a snap fit arrangement, tongue and groove arrangement, "zip lock®" arrangement, adhesives, VELCRO®, etc. The door 118 preferably provides access to the wound bed "w" to enable the clinician to monitor the status of the wound, change the absorbent layer 106, change the micropump system 108, or apply additional medical treatment to the wound such as growth factors, debriders, or other wound healing agents as needed. Once the desired procedure is completed, the access door 118 would be resealed relative to the top layer 110 to maintain the integrity of the wound dressing 100.

Figure 3:
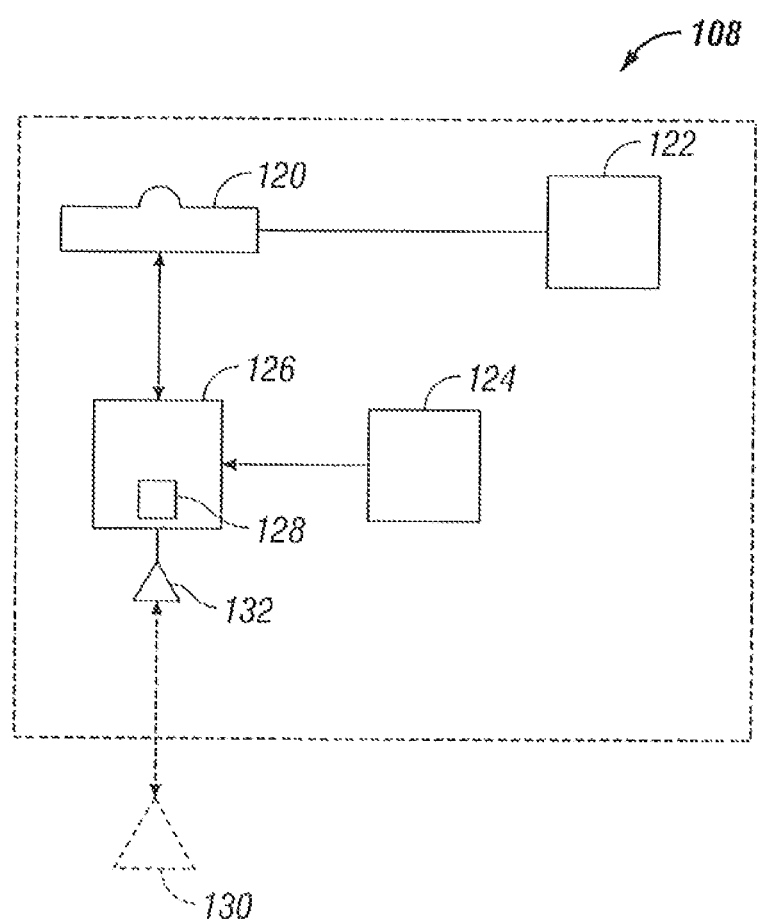
FIG. 3 is a schematic view of the micropump system.

Referring now to the schematic diagram of FIG. 3, in conjunction with FIGS. 1 and 2, the micropump system 108 will be discussed. The micropump system 108 includes a miniature pump or micropump 120 with a length ranging from about 1 to 3 inches and a relatively small diameter, preferably, no greater than about one inch. The micropump 120 may be any type of pump that is biocompatible and maintains or draws adequate and therapeutic vacuum levels. The micropump 120 may be embedded within the absorbent layer 106 or mounted to the layer 106, or alternatively associated within the confines of the wound dressing 100. "Therapeutic vacuum levels" as used herein refers to a vacuum level that draws wound fluid and exudate away from the wound bed. Preferably, the vacuum level to be achieved is in a range between about 75 mmHg and about 125 mmHg. The micropump 120 may be disposable, removable, reusable, and/or rechargeable. Typically, the micropump 120 is a pump of the diaphragmatic or peristaltic type, or the like, in which the moving part(s) draw exudate out of the wound bed into the wound dressing by creating areas or zones of decreased pressure e.g., vacuum zones with the wound dressing 100. This area of decreased pressure preferably communicates with the wound bed "w" to facilitate removal of the fluids therefrom and into the absorbent layer 106. The micropump 120 may be actuated by any means known by those skilled in the art. In a preferred embodiment of the present disclosure, the micropump 120 is a peristaltic pump. One suitable micropump is manufactured by Piab Vacuum Products in Hingham, Mass. Preferably, the peristaltic pump produces subatmospheric pressure ranging from about 20 mmHg to about 500 mmHg.

The micropump system 108 preferably includes an internal self contained battery source 122, a pressure sensor or transducer 124 to monitor pressure adjacent the micropump 120 or selected locations displaced from the micropump 120, and regulation or control means 126. The control means 126 may incorporate a motor controller/driver 128 including processing and drive circuitry to control or vary the drive voltage to the motor of the micropump 120 responsive to the pressure sensed by the pressure sensor 124. The output of the motor of the micropump 120 may be increased or decreased, or initiated or discontinued, as controlled by the control means 126. The pressure sensor 124 would also provide information to assist in detecting a leak in the wound closure apparatus 10 if the optimal subatmospheric pressure is not achieved. The regulation or control means 126 may also have an alarm such as a visual, audio or tactile sensory alarm (e.g., vibratory etc.) to indicate to the user when specific conditions have been met (e.g., the desired vacuum level or loss of vacuum).

The micropump system 108 is preferably adapted for implantation within the wound dressing 100, i.e., it is an implantable self-contained unit. The battery source 122 and control means 126 may be built into the housing of the micropump 120. The pressure sensor 124 may be mounted to the external surface of the housing of the micropump 120 or communicate through a port in the housing. The pressure sensor 124 may also be displaced from the housing of the micropump 118, e.g., embedded within the absorbent layer 106 at a location displaced from the micropump 120, and connected to the control means 126 through an electrical connection. The micropump 120 and battery 122 may be disposable or rechargeable. Preferably, the micropump system 108 is entirely disposable, e.g., after a single use, and is disposed of along with the absorbent layer 106 of the wound dressing 100. Alternatively, the micropump system 108 may be removed or disconnected from the absorbent layer 106 and reinstalled into another absorbent layer 106 for placement within the wound closure 100.

It is also envisioned that the micropump system 108 may be externally controlled via radio transmitter means. In this alternate embodiment, an external radio frequency (RF) transmitter or antenna 130 (shown in phantom on FIG. 3) may send/receive signals to a receiving transmitter 132 associated with the control means 126 to operate the control means to control functioning of the micropump system 108. One skilled in the art may readily adapt the micropump system 108 to operate via remote radio frequency (RF) means. The micropump system 108 may incorporate circuitry to communicate with a computer, e.g., a hand-held PALM device.

Figure 4:
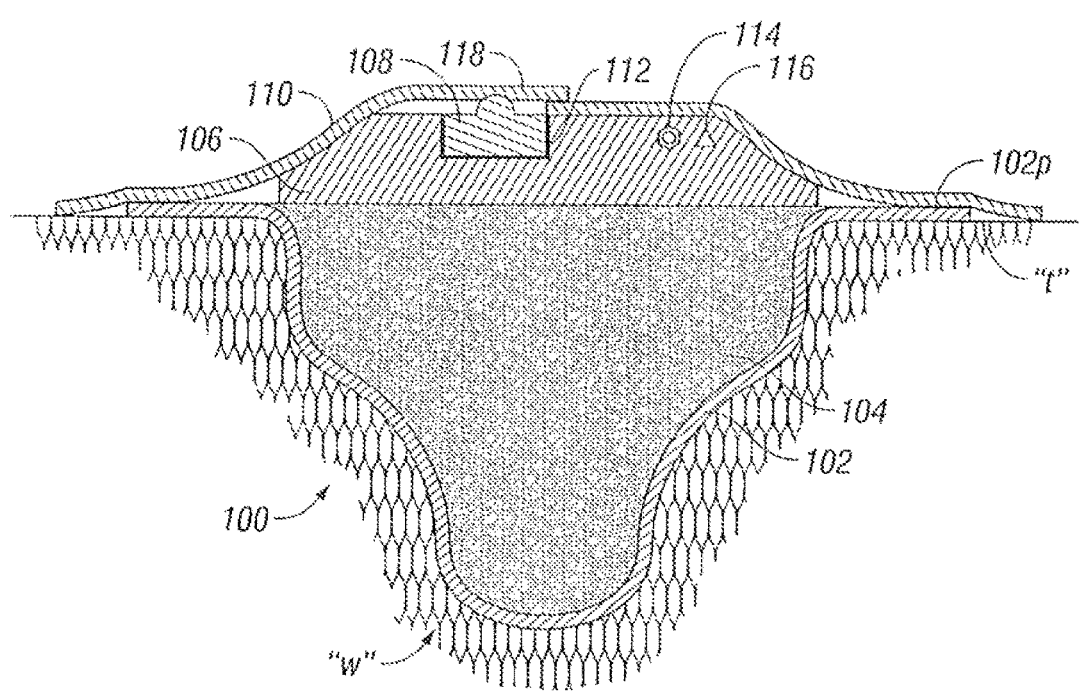
FIG. 4 is a view similar to the view of FIG. 2 illustrating the wound dressing in a contracted condition when subjected to subatmospheric pressure generated by the micropump system.

In use, the wound dressing 100 is positioned within the wound bed "w" as shown in FIG. 2. Thereafter, the micropump 120 is initiated to create a zone of subatmospheric pressure (i.e., a state of vacuum) within the wound dressing 100. The micropump 120 may be initiated via a manual switch associated with the control means 126, or may be started via the pressure sensor 124 which detects the lack of subatmospheric pressure within the wound dressing 100 and sends a corresponding signal to the control means 126. The control means 126, in turn, activates the micropump 120. As the subatmospheric pressure within the wound closure 100 increases, the top layer 110 collapses to the position depicted in FIG. 4. Once the desired level of subatmospheric pressure is achieved as detected by, e.g., the pressure sensor 124, the pressure sensor 124 sends a signal to the control means 126. The control means 126 may either terminate operation of the micropump 120 or alternatively vary the speed or output (e.g., decrease) of the micropump 120. In the vacuum state, wound fluid and exudates are drawn into the absorbent layer 106 to be collected therein. After a period of time, the wound dressing 100 may lose its vacuum state as detected by the pressure sensor 124. Visual confirmation of the loss of vacuum state may also be ascertained by viewing the vacuum indicator 114 through the top layer 110. When the loss of a desired vacuum level is achieved, the pressure sensor 124 sends a signal to the control means 126 to activate or increase the output of the micropump 120. This process may continue several times during wound healing.

Figure 5:
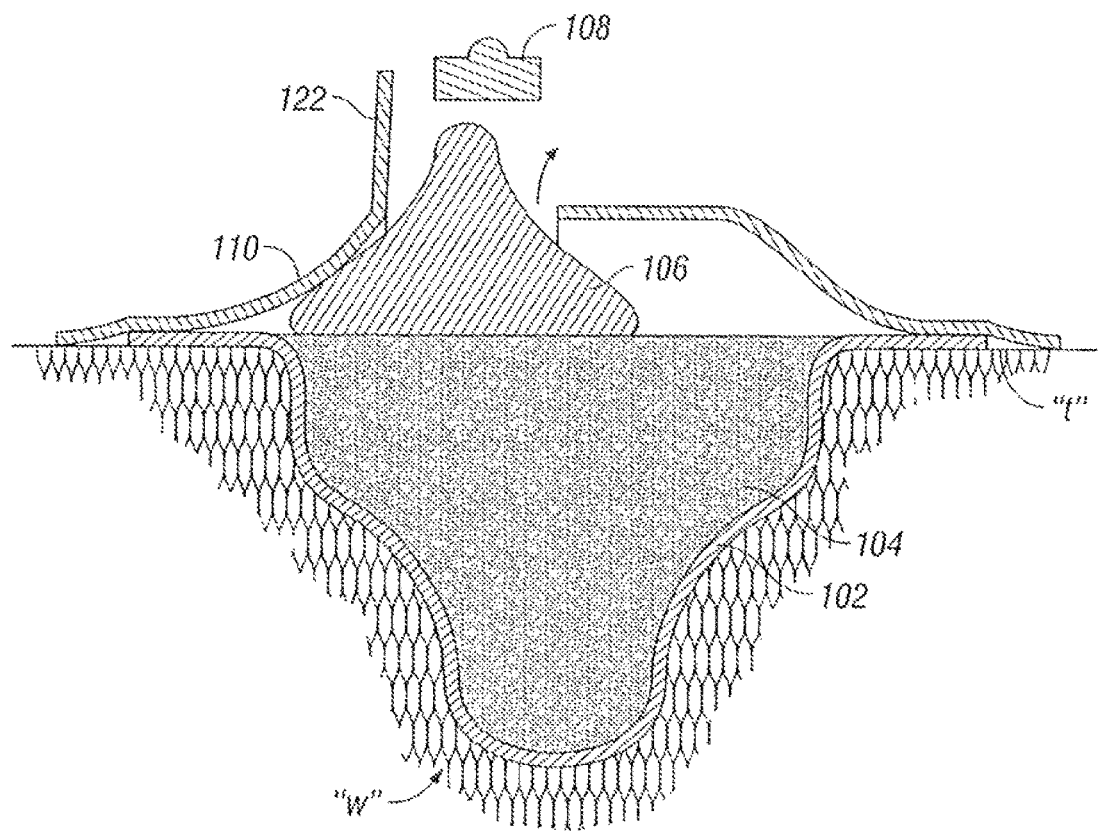
FIG. 5 is a view illustrating the access door of the wound dressing in an open condition to permit removal of the absorbent layer and/or micropump system.

Once the absorbent layer 106 is fully saturated as detected by viewing the saturation indicator 116 through the top layer 110, the access door 118 may be opened as shown in FIG. 5. The absorbent layer 106 and the micropump system 108 may be removed through the door. As discussed, a new absorbent layer 106 and/or new micropump system 108 subsequently may be introduced through the door 118 and installed within the wound dressing 100.

Figure 6:
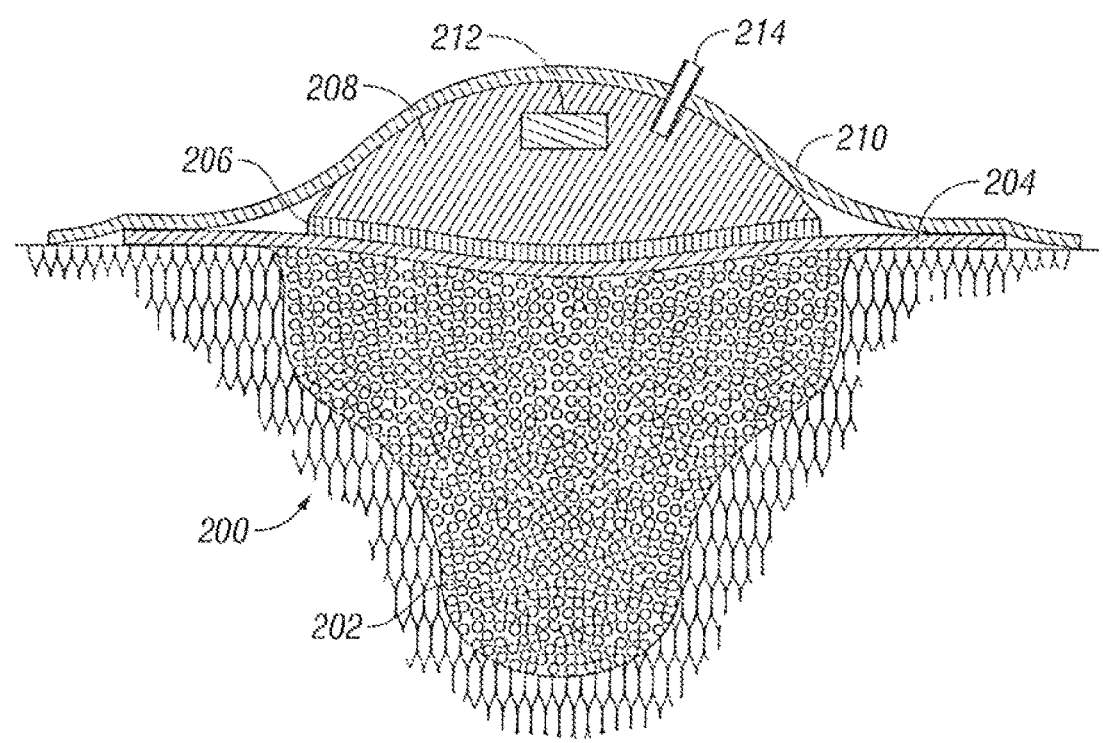
FIG. 6 is a side cross-sectional view of another embodiment of the self contained wound dressing and micropump system of the present disclosure.

FIG. 6 illustrates an alternate embodiment of the present disclosure. In accordance with this embodiment, wound dressing 200 includes a bead packing 202, contact layer 204, capillary layer 206, packing layer 208 and occlusive layer 210. Bead packing 202 may incorporate a plurality of antimicrobial beads, beads with growth factors, medicaments, antibiotics, analgesics, and healing factors such as vitamins, growth factors, nutrients and the like. These beads are preferably non-adherent and may be bioabsorbable over a predetermined period of time. Alternatively, the beads may be non-absorbable. The beads may be injectable into the wound site. Multiple applications of the beads are also contemplated.

Alternatively, contact layer 204 may be similar to the base layer 102 discussed hereinabove and is preferably porous. Capillary layer 206 includes a plurality of capillary fibers defining microchannels that permit controlled directional flow of a liquid, e.g., to permit drainage of the exudates from the wound. These channels formed in sheets, films, or tubes may be uniform in dimension or random and extend along the length of the layer. The microchannels desirably permit fluid flow in one direction, i.e., away from the wound for wound drainage, for example, similar to dialysis filters. Packing layer 208 and micropump 212 are substantially similar to their counterparts discussed hereinabove. Occlusive layer 210 may comprise a silicon or hydrogel material that can be adherent on the skin contact side and non-adherent to the outer side, and is preferably adherent in moist/oily environments. The occlusive layer 210 may also be a film forming liquid material which is dispensed from a spray mechanism for application over the dressing with the same surface characteristics described above. Wound dressing 200 may further incorporate a supplemental port 214 for connection to an external drainage canister or such as a drainage bag.

Figure 7:
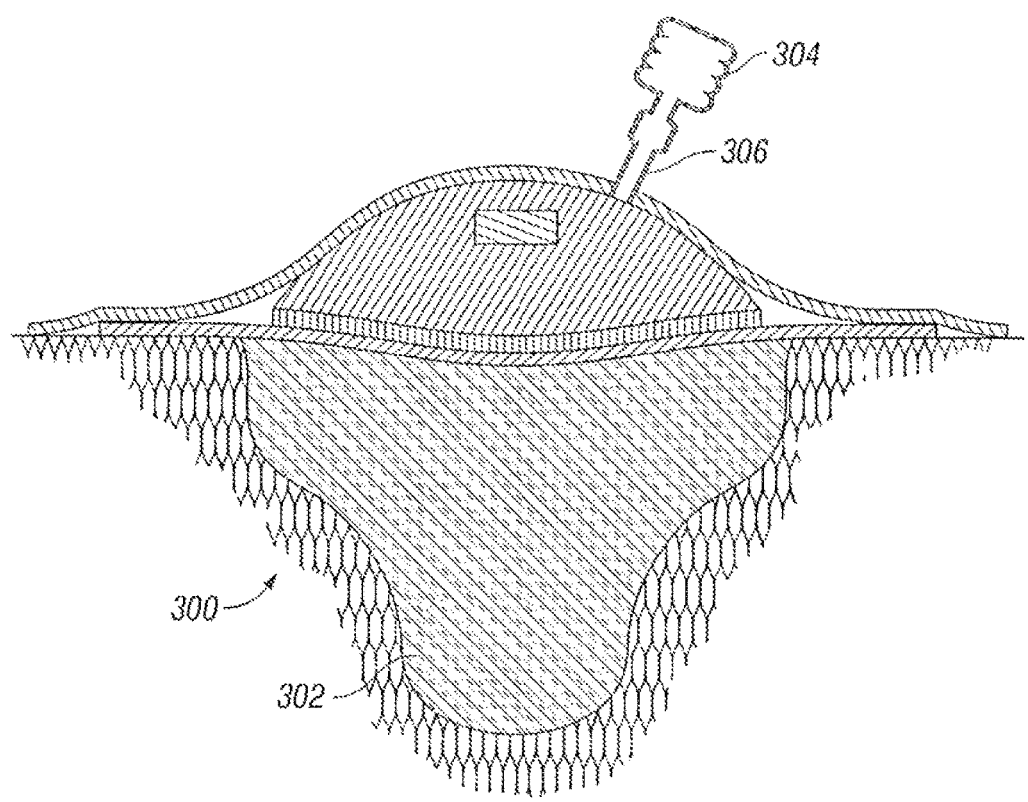
FIG. 7 is a side cross-sectional view of yet another embodiment of the self contained wound dressing and micropump system of the present disclosure.

FIG. 7 illustrates an alternate wound dressing 300 which incorporates biocompatible foam 302 in lieu of the bead layer. The foam 302 may be a resilient, liquid absorbent, porous, polymer-based foam. The foam 302 may be a dispensable liquid which at least partially solidifies to a crystal-like arrangement defining hollow tubes to allow exudates drainage. The foam 302 is dispensed within the wound bed and is potentially collapsible to expel air from the foam channels. The foam 302 may be an expandable hydrophilic foam which is capable of absorbing fluid from a wound and maintain the wound bed moist. The hollow tubes or voids defined by the foam 302 also provide a means to conduct electricity, heat, cold, and ultrasound. The hollow tubes or voids also provide a bioactive scaffold for tissue growth. Wound dressing 300 further includes an accordion style bag or canister 304 connected to the interior of dressing 300 through port 306. Canister 304 may be compressed to impart energy to the wound exudates to drain the fluid into the bag. One suitable system is disclosed in commonly assigned U.S. Pat. No. 5,549,584 to Gross, the entire contents of which are hereby incorporated herein by reference. A one-way valve may be incorporated into the port leading to canister 304 if desired.

It is further contemplated that the wound dressing apparatus may incorporate external means or applications to stimulate tissue growth and/or healing. For example, an ultrasonic transducer may be incorporated into the wound dressing apparatus to impart mechanical energy for the treatment of the tissue such as, for instance, directing thermal or vibratory energy on the wound area and/or introducing various drugs into the human body through the skin. Other sensor types are also contemplated for incorporation into the wound dressing apparatus including oxygen, chemical, microbial, perfusion and/or temperature sensors. The detection of oxygen adjacent the wound area would assist the clinician in determining the status of wound healing. The presence of an elevated temperature may be indicative of an infection.

While the disclosure has been illustrated and described, it is not intended to be limited to the details shown, since various modifications and substitutions can be made without departing in any way from the spirit of the present disclosure. For example, it is envisioned the subject matter of the commonly assigned patent application filed concurrently herewith under Express Mail Certificate No. EL 985194499 US, and which claims priority to provisional application No. 60/714,805, filed on Sep. 7, 2006, and the subject matter of the commonly assigned patent application filed concurrently herewith under Express Mail Certificate No. EL 985194539 US, and which claims priority to provisional application No. 60/714,912, filed on Sep. 7, 2006, (the entire contents of each application being incorporated herein) may be incorporated into the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A negative pressure wound treatment apparatus, comprising:
　a wound dressing configured to be positioned over a wound site, the wound dressing comprising:
　　a contact layer comprising a plurality of perforations through the contact layer that allow for fluid to pass there through;
　　a capillary layer located above the contact layer configured to allow transmission of fluid away from the wound site;
　　an absorbent layer located above the capillary layer configured to form a reservoir for fluid removed from the wound site, wherein the absorbent layer comprises super absorbent polymer material; and
　　a cover layer located above the absorbent layer;
　a negative pressure source configured to apply negative pressure to the wound site through the perforations in the contact layer and through the capillary layer and configured to draw fluid from the wound site into the absorbent layer; and
　a pressure indicator configured to indicate a level of pressure within the wound dressing.

2. The apparatus according to claim 1, wherein the cover layer comprises a transparent material.

3. The apparatus according to claim 1, wherein the cover layer comprises an adhesive configured to adhere to skin surrounding the wound site.

4. The apparatus according to claim 3, wherein the cover layer does not adhere to the absorbent layer.

5. The apparatus according to claim 1, wherein the capillary layer comprises a plurality of capillary fibers.

6. The apparatus according to claim 1, wherein the pressure indicator utilizes color to indicate a non-vacuum state.

7. The apparatus according to claim 1, wherein the pressure indicator is located within the wound dressing.

8. The apparatus according to claim 1, further comprising a saturation indicator configured to indicate a level of saturation of the absorbent layer.

9. The apparatus according to claim 1, wherein the negative pressure source is positioned within the wound dressing.

10. The apparatus according to claim 1, wherein the wound dressing further comprises a port connected to the cover layer.

11. The apparatus according to claim 1, further comprising a canister configured to be connected to the wound dressing.

12. A negative pressure wound treatment apparatus, comprising:
　a wound dressing configured to be positioned over a wound site, the wound dressing comprising:
　　a contact layer comprising a plurality of perforations through the contact layer that allow for fluid to pass there through;
　　a capillary layer located above the contact layer configured to allow transmission of fluid away from the wound site;
　　an absorbent layer located above the capillary layer configured to form a reservoir for fluid removed from the wound site, wherein the absorbent layer comprises super absorbent polymer material;
　　a cover layer located above the absorbent layer;
　　a port connected to the cover layer;
　a compressible suction device configured to connect to the port to apply suction through the port to the wound dressing; and
　a color indicator configured to indicate a non-vacuum state within the wound dressing.

13. The apparatus according to claim 12, wherein the cover layer comprises a transparent material.

14. The apparatus according to claim 12, wherein the capillary layer comprises a plurality of capillary fibers.

15. The apparatus according to claim 12, further comprising an adhesive for adhering the wound dressing to skin surrounding the wound.

16. A method of treating a wound, the method comprising:
　positioning a wound dressing over a wound site, the wound dressing comprising:
　　a contact layer comprising a plurality of perforations;
　　a capillary layer located above the contact layer;
　　an absorbent layer located above the capillary layer, wherein the absorbent layer comprises super absorbent polymer material; and
　　a cover layer located above the absorbent layer;
　applying negative pressure to the wound from a negative pressure source, the negative pressure being applied through the perforations in the contact layer and through the capillary layer and configured to draw fluid from the wound site into the absorbent layer; and
　using a pressure indicator to indicate a level of pressure within the wound dressing.

17. The method according to claim 16, wherein the cover layer comprises a transparent material.

18. The method according to claim 16, wherein the capillary layer comprises a plurality of capillary fibers.

19. The method according to claim 16, wherein the pressure indicator indicates a level of pressure using a color.

20. The method according to claim 16, wherein the pressure indicator is located within the wound dressing.

21. The method according to claim 16, further comprising indicating a level of saturation of the absorbent layer with a saturation indicator.

22. The method according to claim 16, wherein the negative pressure source is positioned within the wound dressing.

23. The method according to claim 16, further comprising applying suction through a port connected to the wound cover with a compressible suction device.

24. The method according to claim 16, further comprising providing a canister in fluid communication with the wound dressing.

25. A negative pressure wound treatment apparatus, comprising:
　a wound dressing configured to be positioned over a wound site, the wound dressing comprising:
　　a contact layer comprising a plurality of perforations through the contact layer that allow for fluid to pass there through;
　　a capillary layer located above the contact layer configured to allow transmission of fluid away from the wound site;

an absorbent layer located above the capillary layer configured to form a reservoir for fluid removed from the wound site, wherein the absorbent layer comprises super absorbent polymer material; and a cover layer located above the absorbent layer; and a negative pressure source configured to apply negative pressure to the wound site through the perforations in the contact layer and through the capillary layer and configured to draw fluid from the wound site into the absorbent layer, wherein the negative pressure source is positioned within the wound dressing.

26. The apparatus according to claim 25, wherein the cover layer comprises a transparent material.

27. The apparatus according to claim 25, further comprising a saturation indicator configured to indicate a level of saturation of the absorbent layer.

28. The apparatus according to claim 25, wherein the negative pressure source comprises a miniature pump.

29. The apparatus according to claim 25, wherein the negative pressure source is embedded within the absorbent layer.

30. The apparatus according to claim 25, wherein the absorbent layer is preformed or shaped to accept the negative pressure source.

31. The apparatus according to claim 30, wherein the absorbent layer comprises a recess to accommodate the negative pressure source.

32. The apparatus according to claim 25, wherein the absorbent layer comprises multiple layers of absorbent material.

33. The apparatus according to claim 25, wherein the wound dressing further comprises a color coded pressure indicator wherein a first color on the pressure indicator indicates a first level of pressure within the wound dressing and a second color on the pressure indicator indicates a second level of pressure within the wound dressing.

34. The apparatus according to claim 25, further comprising a battery source, a pressure sensor, and a control means integrated with the negative pressure source positioned within the wound dressing.

35. The apparatus according to claim 25, further comprising a control means configured to control or vary the operation of the negative pressure source in response to the pressure sensed by a pressure sensor.

36. The apparatus according to claim 25, further comprising a manual switch configured to initiate the negative pressure source.

37. A method of treating a wound, the method comprising:
positioning a wound dressing over a wound site, the wound dressing comprising:
a contact layer comprising a plurality of perforations;
a capillary layer located above the contact layer;
an absorbent layer located above the capillary layer, wherein the absorbent layer comprises super absorbent polymer material; and
a cover layer located above the absorbent layer; and
applying negative pressure to the wound from a negative pressure source, the negative pressure being applied through the perforations in the contact layer and through the capillary layer and configured to draw fluid from the wound site into the absorbent layer, wherein the negative pressure source is positioned within the wound dressing.

38. The method according to claim 37, further comprising indicating a level of saturation of the absorbent layer with a saturation indicator.

39. The method according to claim 37, further comprising indicating a pressure within the wound dressing with a color coded pressure indicator, wherein a first color on the pressure indicator indicates a first level of pressure within the wound dressing and a second color on the pressure indicator indicates a second level of pressure within the wound dressing.

40. The method according to claim 37, further comprising providing a battery source, a pressure sensor, and a control means integrated with the negative pressure source positioned within the wound dressing.

41. The method according to claim 37, further comprising controlling or varying operation of the negative pressure source with a control means in response to a pressure sensed by a pressure sensor.

42. The method according to claim 37, further comprising initiating the negative pressure source with a manual switch.

* * * * *